US005391712A

United States Patent [19]

Adams

[11] Patent Number: 5,391,712

[45] Date of Patent: Feb. 21, 1995

[54] NON-HEMOLYTIC STREPTOLYSIN O VARIANTS

[75] Inventor: Craig W. Adams, Corona, Calif.

[73] Assignee: Beckman Instruments, Inc., Fullerton, Calif.

[21] Appl. No.: 752,428

[22] Filed: Aug. 30, 1991

[51] Int. Cl.[6] ........................ C07K 13/00; C07K 15/04

[52] U.S. Cl. .................................... 530/350; 530/825; 435/69.3

[58] Field of Search ............... 530/350, 825; 435/69.3, 435/172.3

[56] References Cited

U.S. PATENT DOCUMENTS 4,925,799 5/1990 Rosenberg ....................... 435/172.3

FOREIGN PATENT DOCUMENTS 2003307 5/1990 Canada .
9006951 6/1990 .

OTHER PUBLICATIONS

Kehoe, M. & Timmus, K.N.; "Cloning and Expression in *Escherichia coli*, of the Streptolysin O Determinant from *Streptococcus Pyogenes*"; *Infec. Imm.* 43:804–810 (1984).

Kehoe, M. A. et al "Nucleotide Sequence of the Streptolysin O (SLO) Gene: Structural Homologies between SLO and Other Membrane–Damaging, Thiol–Activated Toxins"; *Infect. Imm.* 55:3228–3232 (Dec. 1987).

Becker, J. et al. "Nephelometric Determination of Antistreptolysin O." AACC 1991 Meeting, Washington, D.C. (Aug. 1, 1991).

Shatzman, A. R. & Rosenberg, M. "Expression Identification, and Chracterization of Recombinant Gene Products in *Escherichia coli.*" *Methods of Enzymology* 152:661–675 (1987).

Shatzman, A. R. & Rosenberg, M. "The pAS Vector System and Its Application to Heterologous Gene Expression in *Escherichia coli.*" *Hepatology* 7:305–355 (1987).

Degnen, G. A. & Cox E. C. "Conditional Mutator Gene in *Escherichia coli*: Isolation Mapping and Effector Studies." *J. Bacter.* 117:477–487 (1987).

Echols, H. et al. "Mutator Strains of *Escherichia coli, mutD* and *dnaQ*, with defective exonucleolytic editing by DNA polymerase III holoezyme." *PNAS USA* 80:2189–2192 (1983).

Schaaper, R. M. "Mechanisms of mutagenesis in the *Escherichia coli* mutator mutD5: Role of DNA mismatch repair." *PNAS USA* 85:8126–8130 (1986).

Alouf, J. E. "Streptococcal Toxins (Streptolysin O, Streptolysin S, Erythrogenic Toxin)". *Pharmac. Ther.* 11:661–717 (1980).

Geoffroy et al., "Alveolysin, The Thiol Activated Toxin . . . ", J. Bact. 172(12): 7301–7305, Dec. 1990.

*Primary Examiner*—Stephen G. Walsh
*Attorney, Agent, or Firm*—William H. May; P.R. Harder; Janis C. Henry

[57] ABSTRACT

Disclosed herein are variant versions of Streptolysin O produced by recombinant DNA techniques. In an embodiment, the variant is soluble upon expression and has a specific hemolytic activity of about 14 hemolytic units per milligram.

1 Claim, 8 Drawing Sheets

ATG GAT CCG TCA GAA GAC AAA AAA AAG AGC GAA GAA GAT CAC ACT GAA 48
GAA ATC AAT GAC AAG ATT TAT TCA CTA AAT TAT AAT GAG CTT GAA GTA 96
CTT GCT AAA AAT GGT GAA ACC ATT GAA AAT TTT GTT CCT AAA GAA GGC 144
GTT AAG AAA GCT GAT AAA TTT ATT GTC ATT GAA AGA AAG AAA AAA AAT 192
ATC AAC ACT ACA CCA GTC GAT ATT TCC ATC ATT GAC TCT GTC ACT GAT 240
AGG ACC TAT CCA GCA GCC CTT CAG CTG GCT AAT AAA GGT TTT ACC GAA 288
AAC AAA CCA GAC GCG GTA GTC ACC AAG CGA AAC CCA CAA AAA ATC CAT 336
ATT GAT TTA CCA GGT ATG GGA GAC AAA GCA ACG GTT GAG GTC AAT GAC 384
CCT ACC TAT GCC AAT GTT TCA ACA GCT ATT GAT AAT CTT GTT AAC CAA 432
TGG CAT GAT AAT TAT TCT GGT GGT AAT ACG CTT CCT GCC AGA ACA CAA 480
TAT ACT AAA TCA ATG GTA TAT TCT AAG TCA CAG ATT GAA GCA GCT CTA 528
AAT GTT AAT AGC AAA ATC TTA GAT GGT ACT TTA GGC ATT GAT TTC AAG 576
TCG ATT TCA AAA GGT GAA AAG AAG GTG ATG ATT GCA GCA TAC AAG CAA 624
ATT TTT TAC ACC GTA TCA GCA AAC CTT CCT AAT AAT CCT GCG GAT GTG 672
TTT GAT AAA TCA GTG ACC TTT AAA GAG TTG CAA CGA AAA GGT GTC AGC 720
AAT GAA GCT CCG CCA CTC TTT GTG AGT AAC GTA GCC TAT GGT CGA ACT 768
GTT TTT GTC AAA CTA GAA ACA AGT TCT AAA AGT AAT GAT GTT GAA GCG 816
GCC TTT AGT GCA GCT CTA AAA GGA ACA GAT GTT AAA ACT AAT GGA AAA 864
TAC TCT GAT ATC TTA GAA AAT AGC TCA TTT ACA GCT GTC GTT TTA GGA 912
GGA GAT GCT GCA GAG CAC AAT AAG GTA GTC ACA AAA GAC TTT GAT GTT 960
ATT AGA AAC GTT ATC AAA GAC AAT GCT ACC TTC AGT AGA AAA AAC CCA 1008
GCT TAT CCT ATT TCA TAC ACC AGT GTT TTC CTT AAA AAT AAT AAA ATT 1056
GCG GGT GTC AAT AAC AGA ACT GAA TAC GTT GAA ACA ACA TCT ACC GAG 1104
TAC ACT AGT GGA AAA ATT AAC CTG TCT CAT CAA GGC GCG TAT GTT GCT 1152
CAA TAT GAA ATC CTT TGG GAT GAA ATC AAT TAT GAT GAC AAA GGA AAA 1200
GAA GTG ATT ACA AAA CGA CGT TGG GAT AAC AAC TGG TAT AGT AAG ACA 1248
TCA CCA TTT AGC ACA GTT ATC CCA CTA GGA GCT AAT TCA CGA AAT ATA 1296
CGT ATC ATG GCT AGA GAG TGC ACC GGC TTA GCT TGG GAA TGG TGG CGA 1344
AAA GTG ATC GAC GAA AGA GAT GTG AAA CTG TCT AAA GAA ATC AAT GTC 1392
AAC ATC TCA GGA TCA ACC CTG AGC CCA TAT GGT TCG ATT ACT TAT AAG 1440
TAG GAC TGG TTC AAG AGG TTC GTC AAG CAC CTT GAT GCT GCT TAT CTC 1488
TTG AGA TCC CCG GGT AGG CCT AGT TAA CTA GTC GAC 1524

FIG. 1

| | | | | | | | | | | | | | | | |
|---|---|---|---|---|---|---|---|---|---|---|---|---|---|---|---|
| Met | Asp | Pro | Ser | Glu | Asp | Lys | Lys | Lys | Ser | Glu | Glu | Asp | His | Thr | Glu |
| -2 | -1 | | | | | 5 | | | | | 10 | | | | |
| Glu | Ile | Asn | Asp | Lys | Ile | Tyr | Ser | Leu | Asn | Tyr | Asn | Glu | Leu | Glu | Val |
| 15 | | | | | 20 | | | | | 25 | | | | | 30 |
| Leu | Ala | Lys | Asn | Gly | Glu | Thr | Ile | Glu | Asn | Phe | Val | Pro | Lys | Glu | Gly |
| | | | | 35 | | | | | 40 | | | | | 45 | |
| Val | Lys | Lys | Ala | Asp | Lys | Phe | Ile | Val | Ile | Glu | Arg | Lys | Lys | Lys | Asn |
| | | | 50 | | | | | 55 | | | | | 60 | | |
| Ile | Asn | Thr | Thr | Pro | Val | Asp | Ile | Ser | Ile | Ile | Asp | Ser | Val | Thr | Asp |
| | | 65 | | | | | 70 | | | | | 75 | | | |
| Arg | Thr | Tyr | Pro | Ala | Ala | Leu | Gln | Leu | Ala | Asn | Lys | Gly | Phe | Thr | Glu |
| | 80 | | | | | 85 | | | | | 90 | | | | |
| Asn | Lys | Pro | Asp | Ala | Val | Val | Thr | Lys | Arg | Asn | Pro | Gln | Lys | Ile | His |
| 95 | | | | | 100 | | | | | 105 | | | | | 110 |
| Ile | Asp | Leu | Pro | Gly | Met | Gly | Asp | Lys | Ala | Thr | Val | Glu | Val | Asn | Asp |
| | | | | 115 | | | | | 120 | | | | | 125 | |
| Pro | Thr | Tyr | Ala | Asn | Val | Ser | Thr | Ala | Ile | Asp | Asn | Leu | Val | Asn | Gln |
| | | | 130 | | | | | 135 | | | | | 140 | | |
| Trp | His | Asp | Asn | Tyr | Ser | Gly | Gly | Asn | Thr | Leu | Pro | Ala | Arg | Thr | Gln |
| | | 145 | | | | | 150 | | | | | 155 | | | |
| Tyr | Thr | Lys | Ser | Met | Val | Tyr | Ser | Lys | Ser | Gln | Ile | Glu | Ala | Ala | Leu |
| | 160 | | | | | 165 | | | | | 170 | | | | |
| Asn | Val | Asn | Ser | Lys | Ile | Leu | Asp | Gly | Thr | Leu | Gly | Ile | Asp | Phe | Lys |
| 175 | | | | | 180 | | | | | 185 | | | | | 190 |
| Ser | Ile | Ser | Lys | Gly | Glu | Lys | Lys | Val | Met | Ile | Ala | Ala | Tyr | Lys | Gln |
| | | | | 195 | | | | | 200 | | | | | 205 | |
| Ile | Phe | Tyr | Thr | Val | Ser | Ala | Asn | Leu | Pro | Asn | Asn | Pro | Ala | Asp | Val |
| | | | 210 | | | | | 215 | | | | | 220 | | |
| Phe | Asp | Lys | Ser | Val | Thr | Phe | Lys | Glu | Leu | Gln | Arg | Lys | Gly | Val | Ser |
| | | 225 | | | | | 230 | | | | | 235 | | | |
| Asn | Glu | Ala | Pro | Pro | Leu | Phe | Val | Ser | Asn | Val | Ala | Tyr | Gly | Arg | Thr |
| | 240 | | | | | 245 | | | | | 250 | | | | |
| Val | Phe | Val | Lys | Leu | Glu | Thr | Ser | Ser | Lys | Ser | Asn | Asp | Val | Glu | Ala |
| 255 | | | | | 260 | | | | | 265 | | | | | 270 |
| Ala | Phe | Ser | Ala | Ala | Leu | Lys | Gly | Thr | Asp | Val | Lys | Thr | Asn | Gly | Lys |
| | | | | 275 | | | | | 280 | | | | | 285 | |
| Tyr | Ser | Asp | Ile | Leu | Glu | Asn | Ser | Ser | Phe | Thr | Ala | Val | Val | Leu | Gly |
| | | | 290 | | | | | 295 | | | | | 300 | | |
| Gly | Asp | Ala | Ala | Glu | His | Asn | Lys | Val | Val | Thr | Glu | Asp | Phe | Asp | Val |
| | | 305 | | | | | 310 | | | | | 315 | | | |
| Ile | Arg | Asn | Val | Ile | Lys | Asp | Asn | Ala | Thr | Phe | Ser | Arg | Lys | Asn | Pro |
| | 320 | | | | | 325 | | | | | 330 | | | | |
| Ala | Tyr | Pro | Ile | Ser | Tyr | Thr | Ser | Val | Phe | Leu | Lys | Asn | Asn | Lys | Ile |
| 335 | | | | | 340 | | | | | 345 | | | | | 350 |
| Ala | Gly | Val | Asn | Asn | Arg | Thr | Glu | Tyr | Val | Glu | Thr | Thr | Ser | Thr | Glu |
| | | | | 355 | | | | | 360 | | | | | 365 | |
| Tyr | Thr | Ser | Gly | Lys | Ile | Asn | Leu | Ser | His | Gln | Gly | Ala | Tyr | Val | Ala |
| | | | 370 | | | | | 375 | | | | | 380 | | |
| Gln | Tyr | Glu | Ile | Leu | Trp | Asp | Glu | Ile | Asn | Tyr | Asp | Asp | Lys | Gly | Lys |
| | | 385 | | | | | 390 | | | | | 395 | | | |
| Glu | Val | Ile | Thr | Lys | Arg | Arg | Trp | Asp | Asn | Asn | Trp | Tyr | Ser | Lys | Thr |
| | 400 | | | | | 405 | | | | | 410 | | | | |
| Ser | Pro | Phe | Ser | Thr | Val | Ile | Pro | Leu | Gly | Ala | Asn | Ser | Arg | Asn | Ile |
| 415 | | | | | 420 | | | | | 425 | | | | | 430 |
| Arg | Ile | Met | Ala | Arg | Glu | Cys | Thr | Gly | Leu | Ala | Trp | Glu | Trp | Trp | Arg |
| | | | | 435 | | | | | 440 | | | | | 445 | |
| Lys | Val | Ile | Asp | Glu | Arg | Asp | Val | Lys | Leu | Ser | Lys | Glu | Ile | Asn | Val |
| | | | 450 | | | | | 455 | | | | | 460 | | |
| Asn | Ile | Ser | Gly | Ser | Thr | Leu | Ser | Pro | Tyr | Gly | Ser | Ile | Thr | Tyr | Lys |
| | | 465 | | | | | 470 | | | | | 475 | | | |

FIG. 2

ATG GAT CCG TCA GAA GAC AAA AAA AAG AGC GAA GAA GAT CAC ACT GAA 48
GAA ATC AAT GAC AAG ATT TAT TCA CTA AAT TAT AAT GAG CTT GAA GTA 96
CTT GCT AAA AAT GGT GAA ACC ATT GAA AAT TTT GTT CCT AAA GAA GGC 144
GTT AAG AAA GCT GAT AAA TTT ATT GTC ATT GAA AGA AAG AAA AAA AAT 192
ATC AAC ACT ACA CCA GTC GAT ATT TCC ATC ATT GAC TCT GTC ACT GAT 240
AGG ACC TAT CCA GCA GCC CTT CAG CTG GCT AAT AAA GGT TTT ACC GAA 288
AAC AAA CCA GAC GCG GTA GTC ACC AAG CGA AAC CCA CAA AAA ATC CAT 336
ATT GAT TTA CCA GGT ATG GGA GAC AAA GCA ACG GTT GAG GTC AAT GAC 384
CCT ACC TAT GCC AAT GTT TCA ACA GCT ATT GAT AAT CTT GTT AAC CAA 432
TGG CAT GAT AAT TAT TCT GGT GGT AAT ACG CTT CCT GCC AGA ACA CAA 480
TAT ACT GAA TCA ATG GTA TAT TCT AAG TCA CAG ATT GAA GCA GCT CTA 528
AAT GTT AAT AGC AAA ATC TTA GAT GGT ACT TTA GGC ATT GAT TTC AAG 576
TCG ATT TCA AAA GGT GAA AAG AAG GTG ATG ATT GCA GCA TAC AAG CAA 624
ATT TTT TAC ACC GTA TCA GCA AAC CTT CCT AAT AAT CCT GCG GAT GTG 672
TTT GAT AAA TCA GTG ACC TTT AAA GAG TTG CAA CGA AAA GGT GTC AGC 720
AAT GAA GCT CCG CCA CTC TTT GTG AGT AAC GTA GCC TAT GGT CGA ACT 768
GTT TTT GTC AAA CTA GAA ACA AGT TCT AAA AGT AAT GAT GTT GAA GCG 816
GCC TTT AGT GCA GCT CTA AAA GGA ACA GAT GTT AAA ACT AAT GGA AAA 864
TAC TCT GAT ATC TTA GAA AAT AGC TCA TTT ACA GCT GTC GTT TTA GGA 912
GGA GAT GCT GCA GAG CAC AAT AAG GTA GTC ACA AAA GAC TTT GAT GTT 960
ATT AGA AAC GTT ATC AAA GAC AAT GCT ACC TTC AGT AGA AAA AAC CCA 1008
GCT TAT CCT ATT TCA TAC ACC AGT GTT TTC CTT AAA AAT AAT AAA ATT 1056
GCG GGT GTC AAT AAC AGA ACT GAA TAC GTT GAA ACA ACA TCT ACC GAG 1104
TAC ACT AGT GGA AAA ATT AAC CTG TCT CAT CAA GGC GCG TAT GTT GCT 1152
CAA TAT GAA ATC CTT TGG GAT GAA ATC AAT TAT GAT GAC AAA GGA AAA 1200
GAA GTG ATT ACA AAA CGA CGT TGG GAT AAC AAC TGG TAT AGT AAG ACA 1248
TCA CCA TTT AGC ACA GTT ATC CCA CTA GGA GCT AAT TCA CGA AAT ATA 1296
CGT ATC ATG GCT AGA GAG TGC ACC GGC TTA GCT TGG GAA TGG TGG CGA 1344
AAA GTG ATC GAC GAA AGA GAT GTG AAA CTG TCT AAA GAA ATC AAT GTC 1392
AAC ATC TCA GGA TCA ACC CTG AGC CCA TAT GGT TCG ATT ACT TAT AAG 1440
TAG GAC TGG TTC AAG AGG TTC GTC AAG CAC CTT GAT GCT GCT TAT CTC 1488
TTG AGA TCC CCG GGT AGG CCT AGT TAA CTA GTC GAC 1524

FIG. 3

| | | | | | | | | | | | | | | | |
|---|---|---|---|---|---|---|---|---|---|---|---|---|---|---|---|
| Met | Asp | Pro | Ser | Glu | Asp | Lys | Lys | Lys | Ser | Glu | Glu | Asp | His | Thr | Glu |
| -2 | -1 | | | | | 5 | | | | | 10 | | | | |
| Glu | Ile | Asn | Asp | Lys | Ile | Tyr | Ser | Leu | Asn | Tyr | Asn | Glu | Leu | Glu | Val |
| 15 | | | | | 20 | | | | | 25 | | | | | 30 |
| Leu | Ala | Lys | Asn | Gly | Glu | Thr | Ile | Glu | Asn | Phe | Val | Pro | Lys | Glu | Gly |
| | | | | 35 | | | | | 40 | | | | | 45 | |
| Val | Lys | Lys | Ala | Asp | Lys | Phe | Ile | Val | Ile | Glu | Arg | Lys | Lys | Lys | Asn |
| | | | 50 | | | | | 55 | | | | | 60 | | |
| Ile | Asn | Thr | Thr | Pro | Val | Asp | Ile | Ser | Ile | Ile | Asp | Ser | Val | Thr | Asp |
| | | 65 | | | | | 70 | | | | | 75 | | | |
| Arg | Thr | Tyr | Pro | Ala | Ala | Leu | Gln | Leu | Ala | Asn | Lys | Gly | Phe | Thr | Glu |
| | 80 | | | | | 85 | | | | | 90 | | | | |
| Asn | Lys | Pro | Asp | Ala | Val | Val | Thr | Lys | Arg | Asn | Pro | Gln | Lys | Ile | His |
| 95 | | | | | 100 | | | | | 105 | | | | | 110 |
| Ile | Asp | Leu | Pro | Gly | Met | Gly | Asp | Lys | Ala | Thr | Val | Glu | Val | Asn | Asp |
| | | | | 115 | | | | | 120 | | | | | 125 | |
| Pro | Thr | Tyr | Ala | Asn | Val | Ser | Thr | Ala | Ile | Asp | Asn | Leu | Val | Asn | Gln |
| | | | 130 | | | | | 135 | | | | | 140 | | |
| Trp | His | Asp | Asn | Tyr | Ser | Gly | Gly | Asn | Thr | Leu | Pro | Ala | Arg | Thr | Gln |
| | | 145 | | | | | 150 | | | | | 155 | | | |
| Tyr | Thr | Glu | Ser | Met | Val | Tyr | Ser | Lys | Ser | Gln | Ile | Glu | Ala | Ala | Leu |
| | 160 | | | | | 165 | | | | | 170 | | | | |
| Asn | Val | Asn | Ser | Lys | Ile | Leu | Asp | Gly | Thr | Leu | Gly | Ile | Asp | Phe | Lys |
| 175 | | | | | 180 | | | | | 185 | | | | | 190 |
| Ser | Ile | Ser | Lys | Gly | Glu | Lys | Lys | Val | Met | Ile | Ala | Ala | Tyr | Lys | Gln |
| | | | | 195 | | | | | 200 | | | | | 205 | |
| Ile | Phe | Tyr | Thr | Val | Ser | Ala | Asn | Leu | Pro | Asn | Asn | Pro | Ala | Asp | Val |
| | | | 210 | | | | | 215 | | | | | 220 | | |
| Phe | Asp | Lys | Ser | Val | Thr | Phe | Lys | Glu | Leu | Gln | Arg | Lys | Gly | Val | Ser |
| | | 225 | | | | | 230 | | | | | 235 | | | |
| Asn | Glu | Ala | Pro | Pro | Leu | Phe | Val | Ser | Asn | Val | Ala | Tyr | Gly | Arg | Thr |
| | 240 | | | | | 245 | | | | | 250 | | | | |
| Val | Phe | Val | Lys | Leu | Glu | Thr | Ser | Ser | Lys | Ser | Asn | Asp | Val | Glu | Ala |
| 255 | | | | | 260 | | | | | 265 | | | | | 270 |
| Ala | Phe | Ser | Ala | Ala | Leu | Lys | Gly | Thr | Asp | Val | Lys | Thr | Asn | Gly | Lys |
| | | | | 275 | | | | | 280 | | | | | 285 | |
| Tyr | Ser | Asp | Ile | Leu | Glu | Asn | Ser | Ser | Phe | Thr | Ala | Val | Val | Leu | Gly |
| | | | 290 | | | | | 295 | | | | | 300 | | |
| Gly | Asp | Ala | Ala | Glu | His | Asn | Lys | Val | Val | Thr | Glu | Asp | Phe | Asp | Val |
| | | 305 | | | | | 310 | | | | | 315 | | | |
| Ile | Arg | Asn | Val | Ile | Lys | Asp | Asn | Ala | Thr | Phe | Ser | Arg | Lys | Asn | Pro |
| | 320 | | | | | 325 | | | | | 330 | | | | |
| Ala | Tyr | Pro | Ile | Ser | Tyr | Thr | Ser | Val | Phe | Leu | Lys | Asn | Asn | Lys | Ile |
| 335 | | | | | 340 | | | | | 345 | | | | | 350 |
| Ala | Gly | Val | Asn | Asn | Arg | Thr | Glu | Tyr | Val | Glu | Thr | Thr | Ser | Thr | Glu |
| | | | | 355 | | | | | 360 | | | | | 365 | |
| Tyr | Thr | Ser | Gly | Lys | Ile | Asn | Leu | Ser | His | Gln | Gly | Ala | Tyr | Val | Ala |
| | | | 370 | | | | | 375 | | | | | 380 | | |
| Gln | Tyr | Glu | Ile | Leu | Trp | Asp | Glu | Ile | Asn | Tyr | Asp | Asp | Lys | Gly | Lys |
| | | 385 | | | | | 390 | | | | | 395 | | | |
| Glu | Val | Ile | Thr | Lys | Arg | Arg | Trp | Asp | Asn | Asn | Trp | Tyr | Ser | Lys | Thr |
| | 400 | | | | | 405 | | | | | 410 | | | | |
| Ser | Pro | Phe | Ser | Thr | Val | Ile | Pro | Leu | Gly | Ala | Asn | Ser | Arg | Asn | Ile |
| 415 | | | | | 420 | | | | | 425 | | | | | 430 |
| Arg | Ile | Met | Ala | Arg | Glu | Cys | Thr | Gly | Leu | Ala | Trp | Glu | Trp | Trp | Arg |
| | | | | 435 | | | | | 440 | | | | | 445 | |
| Lys | Val | Ile | Asp | Glu | Arg | Asp | Val | Lys | Leu | Ser | Lys | Glu | Ile | Asn | Val |
| | | | 450 | | | | | 455 | | | | | 460 | | |
| Asn | Ile | Ser | Gly | Ser | Thr | Leu | Ser | Pro | Tyr | Gly | Ser | Ile | Thr | Tyr | Lys |
| | | 465 | | | | | 470 | | | | | 475 | | | |

FIG. 4

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
( A ) LENGTH: 1524 base pairs
( B ) TYPE: Nucleic acid
( C ) STRANDEDNESS: single
( D ) TOPOLOGY: linear ( i i ) MOLECULE TYPE: genomic DNA ( v i ) ORIGINAL SOURCE:
( A ) ORGANISM: Streptococcus pyogenes ( v i i ) IMMEDIATE SOURCE:
( A ) LIBRARY: genomic
( B ) CLONE: mSLO.3/6

( x i ) SEQUENCE DESCRIPTION: SEQ ID NO: 1:

ATG GAT CCG TCA GAA GAC AAA AAA AAG AGC GAA GAA GAT CAC ACT GAA 48

GAA ATC AAT GAC AAG ATT TAT TCA CTA AAT TAT AAT GAG CTT GAA GTA 96

CTT GCT AAA AAT GGT GAA ACC ATT GAA AAT TTT GTT CCT AAA GAA GGC 144

GTT AAG AAA GCT GAT AAA TTT ATT GTC ATT GAA AGA AAG AAA AAA AAT 192

ATC AAC ACT ACA CCA GTC GAT ATT TCC ATC ATT GAC TCT GTC ACT GAT 240

AGG ACC TAT CCA GCA GCC CTT CAG CTG GCT AAT AAA GGT TTT ACC GAA 288

AAC AAA CCA GAC GCG GTA GTC ACC AAG CGA AAC CCA CAA AAA ATC CAT 336

-continued

ATT GAT TTA CCA GGT ATG GGA GAC AAA GCA ACG GTT GAG GTC AAT GAC 384

CCT ACC TAT GCC AAT GTT TCA ACA GCT ATT GAT AAT CTT GTT AAC CAA 432

TGG CAT GAT AAT TAT TCT GGT GGT AAT ACG CTT CCT GCC AGA ACA CAA 480

TAT ACT AAA TCA ATG GTA TAT TCT AAG TCA CAG ATT GAA GCA GCT CTA 528

AAT GTT AAT AGC AAA ATC TTA GAT GGT ACT TTA GGC ATT GAT TTC AAG 576

TCG ATT TCA AAA GGT GAA AAG AAG GTG ATG ATT GCA GCA TAC AAG CAA 624

ATT TTT TAC ACC GTA TCA GCA AAC CTT CCT AAT AAT CCT GCG GAT GTG 672

TTT GAT AAA TCA GTG ACC TTT AAA GAG TTG CAA CGA AAA GGT GTC AGC 720

AAT GAA GCT CCG CCA CTC TTT GTG AGT AAC GTA GCC TAT GGT CGA ACT 768

GTT TTT GTC AAA CTA GAA ACA AGT TCT AAA AGT AAT GAT GTT GAA GCG 816

GCC TTT AGT GCA GCT CTA AAA GGA ACA GAT GTT AAA ACT AAT GGA AAA 864

TAC TCT GAT ATC TTA GAA AAT AGC TCA TTT ACA GCT GTC GTT TTA GGA 912

GGA GAT GCT GCA GAG CAC AAT AAG GTA GTC ACA AAA GAC TTT GAT GTT 960

ATT AGA AAC GTT ATC AAA GAC AAT GCT ACC TTC AGT AGA AAA AAC CCA 1008

GCT TAT CCT ATT TCA TAC ACC AGT GTT TTC CTT AAA AAT AAT AAA ATT 1056

GCG GGT GTC AAT AAC AGA ACT GAA TAC GTT GAA ACA ACA TCT ACC GAG 1104

TAC ACT AGT GGA AAA ATT AAC CTG TCT CAT CAA GGC GCG TAT GTT GCT 1152

CAA TAT GAA ATC CTT TGG GAT GAA ATC AAT TAT GAT GAC AAA GGA AAA 1200

GAA GTG ATT ACA AAA CGA CGT TGG GAT AAC AAC TGG TAT AGT AAG ACA 1248

TCA CCA TTT AGC ACA GTT ATC CCA CTA GGA GCT AAT TCA CGA AAT ATA 1296

CGT ATC ATG GCT AGA GAG TGC ACC GGC TTA GCT TGG GAA TGG TGG CGA 1344

AAA GTG ATC GAC GAA AGA GAT GTG AAA CTG TCT AAA GAA ATC AAT GTC 1392

AAC ATC TCA GGA TCA ACC CTG AGC CCA TAT GGT TCG ATT ACT TAT AAG 1440

TAG GAC TGG TTC AAG AGG TTC GTC AAG CAC CTT GAT GCT GCT TAT CTC 1488

TTG AGA TCC CCG GGT AGG CCT AGT TAA CTA GTC GAC 1524

( 2 ) INFORMATION FOR SEQ ID NO: 2:

( i ) SEQUENCE CHARACTERISTICS:
( A ) LENGTH: 480 amino acids
( B ) TYPE: Amino Acid
( D ) TOPOLOGY: linear ( i i ) MOLECULE TYPE: protein ( i x ) FEATURE:
( A ) NAME/KEY: Signal sequence
( B ) LOCATION: amino acid 98 to amino acid 571 of SLO (except for mutation at amino acid 304 of following sequence)
( C ) IDENTIFICATION METHOD: experimentally determined based upon production of soluble, non- hemolytically active SLO from recombinant vector
( D ) OTHER INFORMATION: Does not lyse red blood cells ( x i ) SEQUENCE DESCRIPTION: SEQ ID NO: 2:

Met Asp Pro Ser Glu Asp Lys Lys Lys Ser Glu Glu Asp His Thr Glu
-2 -1 5 10

Glu Ile Asn Asp Lys Ile Tyr Ser Leu Asn Tyr Asn Glu Leu Glu Val
15 20 25 30

Leu Ala Lys Asn Gly Glu Thr Ile Glu Asn Phe Val Pro Lys Glu Gly
35 40 45

-continued

Val Lys Lys Ala Asp Lys Phe Ile Val Ile Glu Arg Lys Lys Lys Asn
50 55 60

Ile Asn Thr Thr Pro Val Asp Ile Ser Ile Ile Asp Ser Val Thr Asp
65 70 75

Arg Thr Tyr Pro Ala Ala Leu Gln Leu Ala Asn Lys Gly Phe Thr Glu
80 85 90

Asn Lys Pro Asp Ala Val Val Thr Lys Arg Asn Pro Gln Lys Ile His
95 100 105 110

Ile Asp Leu Pro Gly Met Gly Asp Lys Ala Thr Val Glu Val Asn Asp
115 120 125

Pro Thr Tyr Ala Asn Val Ser Thr Ala Ile Asp Asn Leu Val Asn Gln
130 135 140

Trp His Asp Asn Tyr Ser Gly Gly Asn Thr Leu Pro Ala Arg Thr Gln
145 150 155

Tyr Thr Lys Ser Met Val Tyr Ser Lys Ser Gln Ile Glu Ala Ala Leu
160 165 170

Asn Val Asn Ser Lys Ile Leu Asp Gly Thr Leu Gly Ile Asp Phe Lys
175 180 185 190

Ser Ile Ser Lys Gly Glu Lys Lys Val Met Ile Ala Ala Tyr Lys Gln
195 200 205

Ile Phe Tyr Thr Val Ser Ala Asn Leu Pro Asn Asn Pro Ala Asp Val
210 215 220

Phe Asp Lys Ser Val Thr Phe Lys Glu Leu Gln Arg Lys Gly Val Ser
225 230 235

Asn Glu Ala Pro Pro Leu Phe Val Ser Asn Val Ala Tyr Gly Arg Thr
240 245 250

Val Phe Val Lys Leu Glu Thr Ser Ser Lys Ser Asn Asp Val Glu Ala
255 260 265 270

Ala Phe Ser Ala Ala Leu Lys Gly Thr Asp Val Lys Thr Asn Gly Lys
275 280 285

Tyr Ser Asp Ile Leu Glu Asn Ser Ser Phe Thr Ala Val Val Leu Gly
290 295 300

Gly Asp Ala Ala Glu His Asn Lys Val Val Thr Lys Asp Phe Asp Val
305 310 315

Ile Arg Asn Val Ile Lys Asp Asn Ala Thr Phe Ser Arg Lys Asn Pro
320 325 330

Ala Tyr Pro Ile Ser Tyr Thr Ser Val Phe Leu Lys Asn Asn Lys Ile
335 340 345 350

Ala Gly Val Asn Asn Arg Thr Glu Tyr Val Glu Thr Thr Ser Thr Glu
355 360 365

Tyr Thr Ser Gly Lys Ile Asn Leu Ser His Gln Gly Ala Tyr Val Ala
370 375 380

Gln Tyr Glu Ile Leu Trp Asp Glu Ile Asn Tyr Asp Asp Lys Gly Lys
385 390 395

Glu Val Ile Thr Lys Arg Arg Trp Asp Asn Asn Trp Tyr Ser Lys Thr
400 405 410

Ser Pro Phe Ser Thr Val Ile Pro Leu Gly Ala Asn Ser Arg Asn Ile
415 420 425 430

Arg Ile Met Ala Arg Glu Cys Thr Gly Leu Ala Trp Glu Trp Trp Arg
435 440 445

Lys Val Ile Asp Glu Arg Asp Val Lys Leu Ser Lys Glu Ile Asn Val
450 455 460

Asn Ile Ser Gly Ser Thr Leu Ser Pro Tyr Gly Ser Ile Thr Tyr Lys
465 470 475

-continued ( 2 ) INFORMATION FOR SEQ ID NO:3:

( i ) SEQUENCE CHARACTERISTICS:
( A ) LENGTH: 1524 base pairs
( B ) TYPE: Nucleic acid
( C ) STRANDEDNESS: double
( D ) TOPOLOGY: linear ( i i ) MOLECULE TYPE: genomic DNA ( v ) FRAGMENT TYPE: N-terminal fragment ( v i ) ORIGINAL SOURCE:
( A ) ORGANISM: Streptococcus pyogenes ( v i i ) IMMEDIATE SOURCE:
( A ) LIBRARY: genomic
( B ) CLONE: rSLO.3

( x i ) SEQUENCE DESCRIPTION: SEQ ID NO: 3:

ATG GAT CCG TCA GAA GAC AAA AAA AAG AGC GAA GAA GAT CAC ACT GAA 48

GAA ATC AAT GAC AAG ATT TAT TCA CTA AAT TAT AAT GAG CTT GAA GTA 96

CTT GCT AAA AAT GGT GAA ACC ATT GAA AAT TTT GTT CCT AAA GAA GGC 144

GTT AAG AAA GCT GAT AAA TTT ATT GTC ATT GAA AGA AAG AAA AAA AAT 192

ATC AAC ACT ACA CCA GTC GAT ATT TCC ATC ATT GAC TCT GTC ACT GAT 240

AGG ACC TAT CCA GCA GCC CTT CAG CTG GCT AAT AAA GGT TTT ACC GAA 288

AAC AAA CCA GAC GCG GTA GTC ACC AAG CGA AAC CCA CAA AAA ATC CAT 336

ATT GAT TTA CCA GGT ATG GGA GAC AAA GCA ACG GTT GAG GTC AAT GAC 384

CCT ACC TAT GCC AAT GTT TCA ACA GCT ATT GAT AAT CTT GTT AAC CAA 432

TGG CAT GAT AAT TAT TCT GGT GGT AAT ACG CTT CCT GCC AGA ACA CAA 480

TAT ACT GAA TCA ATG GTA TAT TCT AAG TCA CAG ATT GAA GCA GCT CTA 528

AAT GTT AAT AGC AAA ATC TTA GAT GGT ACT TTA GGC ATT GAT TTC AAG 576

TCG ATT TCA AAA GGT GAA AAG AAG GTG ATG ATT GCA GCA TAC AAG CAA 624

ATT TTT TAC ACC GTA TCA GCA AAC CTT CCT AAT AAT CCT GCG GAT GTG 672

TTT GAT AAA TCA GTG ACC TTT AAA GAG TTG CAA CGA AAA GGT GTC AGC 720

AAT GAA GCT CCG CCA CTC TTT GTG AGT AAC GTA GCC TAT GGT CGA ACT 768

GTT TTT GTC AAA CTA GAA ACA AGT TCT AAA AGT AAT GAT GTT GAA GCG 816

GCC TTT AGT GCA GCT CTA AAA GGA ACA GAT GTT AAA ACT AAT GGA AAA 864

TAC TCT GAT ATC TTA GAA AAT AGC TCA TTT ACA GCT GTC GTT TTA GGA 912

GGA GAT GCT GCA GAG CAC AAT AAG GTA GTC ACA AAA GAC TTT GAT GTT 960

ATT AGA AAC GTT ATC AAA GAC AAT GCT ACC TTC AGT AGA AAA AAC CCA 1008

GCT TAT CCT ATT TCA TAC ACC AGT GTT TTC CTT AAA AAT AAT AAA ATT 1056

GCG GGT GTC AAT AAC AGA ACT GAA TAC GTT GAA ACA ACA TCT ACC GAG 1104

TAC ACT AGT GGA AAA ATT AAC CTG TCT CAT CAA GGC GCG TAT GTT GCT 1152

CAA TAT GAA ATC CTT TGG GAT GAA ATC AAT TAT GAT GAC AAA GGA AAA 1200

GAA GTG ATT ACA AAA CGA CGT TGG GAT AAC AAC TGG TAT AGT AAG ACA 1248

TCA CCA TTT AGC ACA GTT ATC CCA CTA GGA GCT AAT TCA CGA AAT ATA 1296

CGT ATC ATG GCT AGA GAG TGC ACC GGC TTA GCT TGG GAA TGG TGG CGA 1344

AAA GTG ATC GAC GAA AGA GAT GTG AAA CTG TCT AAA GAA ATC AAT GTC 1392

AAC ATC TCA GGA TCA ACC CTG AGC CCA TAT GGT TCG ATT ACT TAT AAG 1440

-continued

```
TAG GAC TGG TTC AAG AGG TTC GTC AAG CAC CTT GAT GCT GCT TAT CTC   1488

TTG AGA TCC CCG GGT AGG CCT AGT TAA CTA GTC GAC                   1524
```

( 2 ) INFORMATION FOR SEQ ID NO:4:

( i ) SEQUENCE CHARACTERISTICS:
( A ) LENGTH: 480 amino acids
( B ) TYPE: Amino Acid
( C ) TOPOLOGY: linear ( i i ) MOLECULE TYPE: protein ( i x ) FEATURE:
( A ) NAME/KEY: Signal sequence
( B ) LOCATION: amino acid 97 to amino acid 571 of SLO
( C ) IDENTIFICATION METHOD: experimentally determined based upon production of soluble, hemolytically active SLO from recombinant vector
( D ) OTHER INFORMATION: Lyses red blood cells ( x i ) SEQUENCE DESCRIPTION: SEQ ID NO: 4:

```
Met Asp Pro Ser Glu Asp Lys Lys Lys Ser Glu Glu Asp His Thr Glu
 -2  -1              5                   10

Glu Ile Asn Asp Lys Ile Tyr Ser Leu Asn Tyr Asn Glu Leu Glu Val
 15                  20                  25                  30

Leu Ala Lys Asn Gly Glu Thr Ile Glu Asn Phe Val Pro Lys Glu Gly
                 35                  40                  45

Val Lys Lys Ala Asp Lys Phe Ile Val Ile Glu Arg Lys Lys Lys Asn
             50                  55                  60

Ile Asn Thr Thr Pro Val Asp Ile Ser Ile Ile Asp Ser Val Thr Asp
         65                  70                  75

Arg Thr Tyr Pro Ala Ala Leu Gln Leu Ala Asn Lys Gly Phe Thr Glu
     80                  85                  90

Asn Lys Pro Asp Ala Val Val Thr Lys Arg Asn Pro Gln Lys Ile His
 95                 100                 105                 110

Ile Asp Leu Pro Gly Met Gly Asp Lys Ala Thr Val Glu Val Asn Asp
                115                 120                 125

Pro Thr Tyr Ala Asn Val Ser Thr Ala Ile Asp Asn Leu Val Asn Gln
            130                 135                 140

Trp His Asp Asn Tyr Ser Gly Gly Asn Thr Leu Pro Ala Arg Thr Gln
        145                 150                 155

Tyr Thr Glu Ser Met Val Tyr Ser Lys Ser Gln Ile Glu Ala Ala Leu
    160                 165                 170

Asn Val Asn Ser Lys Ile Leu Asp Gly Thr Leu Gly Ile Asp Phe Lys
175                 180                 185                 190

Ser Ile Ser Lys Gly Glu Lys Lys Val Met Ile Ala Ala Tyr Lys Gln
                195                 200                 205

Ile Phe Tyr Thr Val Ser Ala Asn Leu Pro Asn Asn Pro Ala Asp Val
            210                 215                 220

Phe Asp Lys Ser Val Thr Phe Lys Glu Leu Gln Arg Lys Gly Val Ser
        225                 230                 235

Asn Glu Ala Pro Pro Leu Phe Val Ser Asn Val Ala Tyr Gly Arg Thr
    240                 245                 250

Val Phe Val Lys Leu Glu Thr Ser Ser Lys Ser Asn Asp Val Glu Ala
255                 260                 265                 270

Ala Phe Ser Ala Ala Leu Lys Gly Thr Asp Val Lys Thr Asn Gly Lys
                275                 280                 285

Tyr Ser Asp Ile Leu Glu Asn Ser Ser Phe Thr Ala Val Val Leu Gly
            290                 295                 300

Gly Asp Ala Ala Glu His Asn Lys Val Val Thr Lys Asp Phe Asp Val
```

-continued 305 310 315

Ile Arg Asn Val Ile Lys Asp Asn Ala Thr Phe Ser Arg Lys Asn Pro
320 325 330

Ala Tyr Pro Ile Ser Tyr Thr Ser Val Phe Leu Lys Asn Asn Lys Ile
335 340 345 350

Ala Gly Val Asn Asn Arg Thr Glu Tyr Val Glu Thr Thr Ser Thr Glu
355 360 365

Tyr Thr Ser Gly Lys Ile Asn Leu Ser His Gln Gly Ala Tyr Val Ala
370 375 380

Gln Tyr Glu Ile Leu Trp Asp Glu Ile Asn Tyr Asp Asp Lys Gly Lys
385 390 395

Glu Val Ile Thr Lys Arg Arg Trp Asp Asn Asn Trp Tyr Ser Lys Thr
400 405 410

Ser Pro Phe Ser Thr Val Ile Pro Leu Gly Ala Asn Ser Arg Asn Ile
415 420 425 430

Arg Ile Met Ala Arg Glu Cys Thr Gly Leu Ala Trp Glu Trp Trp Arg
435 440 445

Lys Val Ile Asp Glu Arg Asp Val Lys Leu Ser Lys Glu Ile Asn Val
450 455 460

Asn Ile Ser Gly Ser Thr Leu Ser Pro Tyr Gly Ser Ile Thr Tyr Lys
465 470 475

NON-HEMOLYTIC STREPTOLYSIN O VARIANTS

A portion of the disclosure of this patent document contains material which is subject to copyright protection. The copyright owner does not object to the reproduction by anyone of the patent document or the patent disclosure, as it appears in the Patent and Trademark Office patent file or records, but otherwise reserves all copyright rights whatsoever.

RELATED APPLICATIONS

The application is related to U.S. Ser. No. 07/752,429, filed Aug. 30, 1991 (Beckman Docket No. 128D-104) entitled "Streptolysin O Derivatives" by Craig W. Adams and Eva Y. Wang, and U.S. Ser. No. 08/109,841, filed Aug. 16, 1993, which is a continuation of 07/753,289, filed Aug. 30, 1991, now abandoned, (Beckman Docket No. 128D-123) entitled "Antibodies to Streptolysin O Derivatives and Variants", by Craig W. Adams and Patty Pang. Both applications are being filed simultaneously herewith, and both are incorporated herein by reference.

FIELD OF THE INVENTION

The present invention is generally related to Streptolysin O and more particularly to Streptolysin O variants produced by recombinant DNA technology.

BACKGROUND OF THE INVENTION

Disclosed herein is a variant version of the antigenic substance, Streptotysin O. Streptolysin O is associated in humans with, for example, rheumatic fever, such that immunodiagnostic assays for evidence of immunological response against Streptolysin O are routinely utilized. The disclosed variant version of Streptolysin O is produced by recombinant DNA techniques, is soluble upon expression, and has substantially no hemolytic activity. Prior to this invention, Streptolysin O could be obtained via the bacteria Streptococcus pyogenes. However, Streptolysin O, in its wild-type form, is a dangerous substance in that it will lyse cells, lyse neutrophils, inhibit lymphocyte transformation, and release histimine from platelets. The toxic and pathogenic properties of Streptolysin O are typically monitored by the lysis of red blood cells.

I. The Genetic Code

The genetic code for a particular protein, such as Streptolysin O (hereinafter "SLO"), depends upon the sequential grouping of three nucleotides, referred to as a "codon," and the arrangement of such codons in relationship to each other.

A "nucleotide" consists of a nucleoside and one or more phosphate groups. A "nucleoside" consists of a nitrogeneous base linked to a pentose sugar. A "pentose" sugar comprises five carbon atoms. In a molecule of deoxytribonucleic acid, or "DNA", the pentose sugar is "deoxyribose," and the nitrogeneous base can be adenine ("A"), guanine ("G"), thymine ("T") or cytosine ("C"). In a molecule of ribonucleic acid, or "RNA" the pentose sugar is "ribose", and the nitrogeneous bases are the same as DNA, except uracil ("U") replaces thymine. Three types of RNA, messenger RNA, or "mRNA", transfer RNA, or "tRNA" and ribosomal, or "rRNA" translate the genetic information encoded in the DNA into, e.g., a polypeptide or a protein. Thus, genetic information is generally transferred as follows: DNA→RNA→protein.

The sequence of the nitrogenous bases of the DNA molecule encodes the genetic information contained in that molecule. The sugar and phosphate groups of the DNA molecule perform a structural role, forming the backbone of a series of DNA molecules, referred to as a DNA "macromolecule." DNA consists of two complementary strands of nucleotide chains, and these strands are held together by (relatively) weak hydrogen bonds. The bases of each DNA molecule bind to each other: A always bonds with T and C always bonds with G. Thus, the sequence 5'-ATCG-3' of a first strand lies immediately opposite a complementary sequence 3'-TAGC-5' on the other strand. This is referred to as "complementary base pairing." The process of complementary base pairing is referred to as "hybridization" and results in the formation of a stable double stranded DNA macromolecule.

Each codon specifies one amino acid. "Amino acids" are the principal components of proteins, and "proteins" are the essential constituents of all living cells. There are 20 natural amino acids. Because there are four nucleotide bases (A, C, G and T) and three nucleotides per codon, there are 64 possible codons ($4^3$). Accordingly, because there are only 20 natural amino acids, most amino acids are specified by more than one codon. This is referred to as "redundancy" or "degeneracy". For example, the codons GCG, GCA, GCT and GCC all encode for the amino acid Alanine.

The codon ATG (Met amino acid codon) is the normal "start" codon. The codons TAA, TAG and TGA, which do not encode for amino acids, are normal "stop" codons. The formation of mRNA is established based upon the start codon of one strand of the double stranded DNA macromolecule such that the resulting single stranded mRNA will have a nucleotide sequence complementary to the sequence of a single strand of the DNA. When a stop codon is reached by the mRNA along the DNA molecule, translation is stopped.

The regions along the DNA macromolecule which are translated from the mRNA are referred to as "exons" for eukaryotes, and "translated regions" for prokaryotes. "Genes" include exons (eukaryotes) and translated regions (prokaryotes). Thus, genes encode for proteins and/or polypeptides. Mammals, for example, are eukaryotes; bacteria, for example, are prokaryotes.

The natural synthesis of protein takes place over a series of several steps. The first step is the formation of an mRNA macromolecule complementary to the DNA macromolecule, as noted above. Thereafter, tRNA is manufactured; the tRNA provides a complementary codon ("anti-codon") for each codon on the mRNA macromolecule. Thereafter, rRNA will catalyze the assembly of the codon-specific amino acids resulting from the mRNA:tRNA into proteins and/or polypeptides.

II. Recombinant DNA Technology

Most proteins are produced naturally in extremely small quantities. The advent of recombinant DNA technology has allowed for the production of large quantities of proteins that were previously only available in such small quantities.

The following describes a "typical" genetic manipulation as it might apply to *Escherichia coli*, a typical bacterial host used for cloning.

In order to isolate, or "clone" a gene a DNA library is constructed from a DNA sequence (referred to as a "genome") using vectors. A "vector" is a small circular molecule of double-stranded DNA that occurs naturally in bacteria, yeast and mammalian cells. Vectors generally comprise the following characteristics: (i) a DNA sequence encoding a selectable "marker" which assures that the vector will be maintained in an appropriate host cell (e.g., *E. coli*); (ii) a controllable transcriptional promoter—by "controllable" is meant that the promoter can be "switched on" by manipulation of, e.g. the environment of the vector; a "promoter" is a region of DNA sequence that when switched on produces large amounts of mRNA from the gene of interest inserted into the vector-different promoters (e.g., lac, trp, tac, etc.) have different rates of mRNA production; (iii) translational control sequences, for example, an appropriately positioned ATG start codon and ribosomal binding site; and (iv) a polylinker; a "polylinker" simplifies the insertion of the gene of interest in the correct orientation within the vector. Vectors can be engineered to provide restriction endonuclease sites on either side of an ATG start codon located on the vector such that the gene of interest can be inserted next to the start codon; this allows for immediate transcription of the gene upon activation of the promoter gene.

A "restriction endonuclease" is an enzyme which cuts the double-stranded DNA at specified sequences of four to eight nucleotides in length, and many restriction endonucleases produce staggered cuts that leave a short, single-stranded tail at the location of the cut. This end is referred to as a "cohesive" or "sticky" end because it can form complementary base pairs with another sticky end. The genome is cleaved (cut-up) by a specified restriction endo-nuclease corresponding to the restriction endo-nuclease used to cut the vector, and the individual pieces of the cleaved genome are inserted into the vector. Randomly cleaving the entire genome of a cell with a specific restriction endo-nuclease is typically referred to as the "shotgun" approach to gene cloning. The shotgun approach can produce an extremely large number of DNA fragments, all of which are inserted into vectors.

The individual pieces of the genome and the vectors, having corresponding sticky ends, are "fused" or "annealed" together to form circular hybrid DNA "plasmids" comprising a portion of the genome and the vector.

The plasmids are then introduced into host cells. There are two types of host cells, "eukaryotic" and "prokaryotic". An example of a eukaryotic host cell is the chinese hamster ovary ("CHO"); an example of a prokaryotic host cell is *E. coli* bacteria. For purposes of the discussion to follow, attention will focus on prokaryotic host cells.

When the plasmids are introduced into the host cell, these cells are referred to as being "transformed" with the plasmids. As the cells grow and divide, the plasmids will similarly replicate to produce copies of the plasmids containing the DNA fragments. Each transformed cell is referred to as a "genomic DNA clone" and the entire collection of transformed cells containing all of the different DNA fragments is referred to as a "genomic DNA library".

In order to determine which genomic DNA clones contain the DNA sequence capable of being copied into a corresponding mRNA, it is necessary to separate or "screen" the genomic DNA clones. There are several ways to accomplish this task including, for example, the use of radioactive DNA probes or evidence of immunoreactivity. Screening can be an extremely labor intensive process because, as noted, the shotgun approach by definition leads to the formation of an extensive number of genomic DNA clones, which must be screened to find potential candidates of interest.

III. Mutations

DNA macromolecules are chemically quite similar to each other. A and G are quite similar in chemical composition, and C, T and U are equally similar. Thus, in a specified sequence, substitutions of an A for a G or a C for a T may occur. When such a substitution occurs within a codon such that the amino acid encoded thereby remains the same, then the substitution can be referred to as a "silent" substitution, i.e., the nucleotides are different but the encoded amino acid is the same. However, other substitutions can alter the amino acid encoded by the codon; when the nucleotide alteration results in a chemically similar amino acid, this is referred to as a "conservative" alteration, while a chemically different amino acid resulting from the alteration is referred to as a "non-conservative" alteration. Non-conservative alterations of amino acids can result in a molecule quite unlike the original protein molecule.

A protein that has had its amino acids altered can be referred to as a "mutant" "mutation" or "variant." Mutations occur naturally and can have positive, negative or neutral consequences on the organism experiencing such a mutation. However, such mutation rates are typically very low, i.e., about $10^{-9}$ to about $10^{-10}$ mutations per base replicated.

IV. Streptolysin O

Streptolysin O ("SLO") has an approximate molecular weight of between about 65,000 and about 70,000 daltons. SLO belongs to a class of oxygen sensitive ("thiol-activated"), cell destroying ("cytolytic") toxin ("cytotoxin") which are produced by gram-positive bacterial species belonging to four different genera (streptococcus, bacillus, clostridium and listeria).

SLO interacts with membrane cholesterol and exerts cytolytic-cytotoxic effects on a broad range of mammalian cells. Additionally, SLO has very potent cardiotoxic properties. One of the toxic and pathogenic properties associated with SLO is its hemolytic activity, i.e. SLO will lyse red blood cells, resulting in the release of hemoglobin. SLO can be lethal to laboratory animals in relatively small doses. Injection of SLO into an animal typically results in its immediate death.

Because SLO is produced by specified bacterial species, when these species "invade" a mammalian host, the SLO released by the bacteria is treated by the host as a foreign protein. SLO, then, is an antigen. "Antigens" are high molecular weight compounds which upon entry into the blood stream of a vertebrate stimulate the transformation of the small lymphocytes of the B-type into lymphoblasts. The lymphoblasts secrete antibodies specific to the antigen stimulator. The antibodies are proteins possessing reactive sites specifically complementary to a reactive feature or site on the stimulating antigen. Antibodies generally have the property of rendering the antigen harmless to the host organism by occupying the immunologically active sites, or "epitopes", on the antigen particles or molecules. Anti-SLO antibodies ("ASO") are therefore produced by the host in response to the secretion of SLO into the host. Approximately 80-85% of individuals with current streptococcal infection or their sequelae (an after effect of a disease or injury) will demonstrate elevated levels of ASO.

Determination of previous and/or current infection by an SLO producing bacteria (*S. pyogenes*) is possible using immunodiagnostic assaying techniques which, e.g., rely upon the hemolytic properties of SLO and the binding of ASO to SLO. Focusing on hemolytic immunodiagnostic assays for SLO, a patient sample is added to a known amount of SLO derived from a source other than the patient and this mixture is added to a known amount of red blood cells such as, for example, rabbit red blood cells. Because SLO has hemolytic properties, it will lyse these red blood cells. However, when ASO binds to SLO, the hemolytic properties of SLO are neutralized. Thus, if the sample is obtained from a patient having current streptococcal infection or their sequelae, there will be elevated levels of ASO in the sample. Accordingly, if the mixture results in high levels of hemolytic activity, this indicates that there is little, if any, ASO in the serum sample (and hence little, if any, infection from the SLO secreting bacteria) because the known quantity of SLO in the mixture is capable of lysing the known quantity of red blood cells in the mixture. If the mixture does not lead to hemolytic activity, this is indicative of an amount of ASO in the sample sufficient to inactivate the known quantity of SLO in the mixture. Investigators refer to such an amount of ASO as a "titer". Typically, an ASO titer of greater than about 300 International Units/ml is indicative of infection by a bacterial source capable of secreting SLO. Other immunodiagnostic assays for determination of infection by SLO secreting bacteria include nephelometric and turbidimetric protocols.

In order to utilize the immunodiagnostic assaying technique outlined above, it is necessary to have access to sufficient SLO to be added to the mixture. One source of SLO is culture broths containing the bacteria *Streptococcus pyegenes* ("*S. pyogenes*"). However, obtaining SLO in this manner is quite difficult and costly: for every liter of the *S. pyogenes* culture broth, only about 0.5 mg of SLO can be expected; the typical media for growing *S. pyogenes* is expensive; *S. pyogenes* is a class 2 pathogen; and SLO obtained in this manner contains many other antigenic materials. Additionally, SLO obtained by this procedure tends to be unstable in liquid form. Accordingly, such SLO preparations are most typically supplied as lyophilized powder in vials. Before use, the lyophilized powder must be reconstituted in a suitable solvent. Unfortunately, such reconstituted SLO will rapidly lose its hemolytic activity and therefore it must be used within a brief period after reconstitution or discarded. This has one notable and negative consequence: it is usually impossible to test individual serum samples as soon as they are obtained. Thus, laboratories which conduct ASO assays based upon hemolytic activity typically store the individual samples until a sufficient number are collected to enable economic use of the lyophilized SLO. This can result in an inordinate delay in obtaining test results.

ASO assays which rely upon nephelometric or turbidimetric protocols need significant amounts of purified SLO. Because of the costs associated with obtaining significant quantities of purified SLO from *S. pyogenes* is expensive, the foregoing hemolytic based assay was the first ASO assay to become commercially available.

Finally, because SLO produced by *S. pyogenes* is by definition wild-type SLO, it is hemolytically active, and therefore must be handled with extreme caution.

Recombinant DNA techniques for obtaining SLO fusion products offer the benefit of obtaining relatively large quantities of such products. Using such technology, it would be possible to avoid the tedious and cost-ineffective aspects of obtaining SLO from *S. pyogenes.* In the co-pending application referenced above, SLO derivatives are disclosed. As used herein, the term "SLO derivative" is an SLO fusion product which is soluble, hemolytically active and which is recognized by ASO. SLO derivatives are designated herein as "rSLO". These SLO derivatives are provided in large quantities, are substantially pure, and maintain hemolytic activity.

It would be beneficial to obtain "variants" of SLO derivatives obtained from such recombinant DNA techniques As used herein, the terms "variant", "mutation" or "mutant" are synonymous. SLO variants are designated herein as "mSLO". An mSLO fusion product would provide several benefits, most notably in the manufacturing of immunodiagnostic assays. This is because such an mSLO fusion might be created which would be recognized by ASO antibodies, but would not have associated therewith the hemolytic activity of wild-type SLO.

SUMMARY OF THE INVENTION

The present invention provides SLO variants. These variants, designated herein as "mSLO", comprise the following characteristics and are broadly defined thereby: (i) recognized by wild-type anti-streptolysin O antibodies (ASO), i.e. comprising at least one epitope characteristic of wild-type Streptolysin O; and (ii) substantially non-hemolytic activity. As used herein, the term "recognized" means capable of being bound by at least one antibody directed against wild-type SLO; the phrase "substantially non-hemolytic activity" means an inability to lyse red blood cells at equivalent titers of wild-type SLO; and "wild-type SLO" is accorded the usual definition associated with such phrase, i.e., SLO that is naturally secreted by a capable bacterial source. "Wild-type SLO", by definition, does not include, e.g., SLO fusion products derived via recombinant DNA techniques.

Another aspect of the invention is directed to a method for making mSLO. The method comprises introducing a soluble, hemolytically active fragment of SLO (e.g., wild type or rSLO) in translational fused or unfused form to a host capable of producing high levels of mutagenic activity, to obtain a mutation fragment candidate; introducing said mutation fragment candidate into an appropriate vector to obtain a plasmid; transformed a host capable of expressing the mutation fragment candidate with the plasmid to obtain a mutation protein candidate; screening said mutation protein candidate for an absence of hemolysis of red blood cells. Preferably, screening of said candidate for solubility is also conducted. As used herein, the phrase "high levels of mutagenic activity" means greater than about $10^{-9}$ to about $10^{-10}$ mutations per base replicated.

Another aspect of the invention includes various kits, such as, for example, test kits for ASO titers, calibrator kits and control kits. A test kit for determining ASO titer comprises mSLO in either liquid or non-liquid form. Most preferably, the mSLO is in liquid form because this allows for ASO titer determination on a per-test sample basis. Calibrator and control kits comprise various concentrations of the mSLO such that calibration and control of ASO titer analysis can be accomplished.

A particularly useful mSLO in accordance with the present disclosure is designated herein as mSLO.3/6. which, in a purified form, has a specific hemolytic activity of about 14 hemolytic units ("HU") per mg.

BRIEF DESCRIPTION OF THE DRAWINGS

FIG. 1 is the nucleic acid sequence of a most preferred embodiment of an SLO variant, designated mSLO.3/6 SEQ ID NO:1;

FIG. 2 is the amino acid sequence of mSLO.3/6 SEQ ID NO:2;

FIG. 3 is the nucleic acid sequence of a most preferred embodiment of an SLO derivative, designated rSLO.3 SEQ ID NO:3;

FIG. 4 is the amino acid sequence of rSLO.3 SEQ ID NO:4.

DETAILED DESCRIPTION OF PREFERRED EMBODIMENTS

Figure 5:
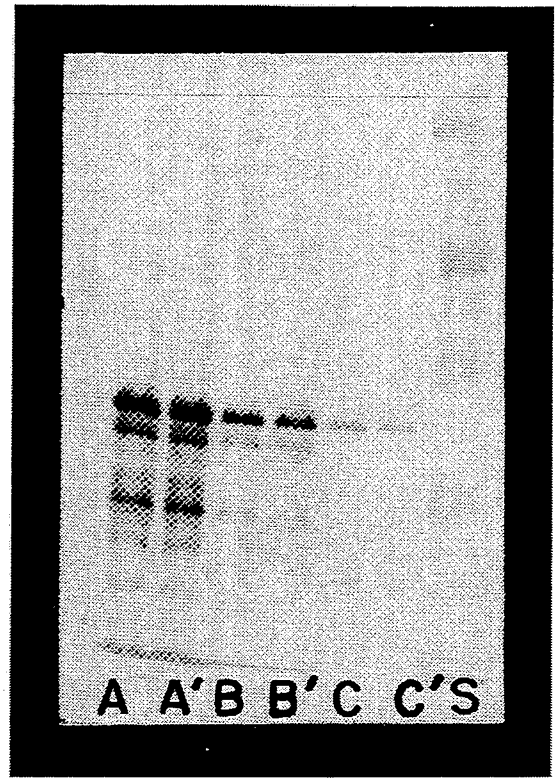
FIG. 5 is the comparative results of a Western blot analysis of supernatant comprising 0.2 μl, 2.0 μl, 10 μl of rSLO.3 and mSLO.3/6.

As used in this disclosure, Streptolysin O variants or "mSLO" comprise the following characteristics and are broadly defined thereby: (i) recognized by wild-type anti-streptolysin O antibodies (ASO); and (ii) substantially non-hemolytic activity. As used herein, the term "recognized" means capable of being bound by at least one antibody directed against wild-type SLO; the phrase "substantially non-hemolytic activity" means an inability to lyse red blood cells at equivalent titers of wild-type SLO; and "wild-type SLO" is accorded the usual definition associated with such phrase, i.e., SLO that is naturally secreted by a bacterial source capable of secreting such protein. Preferably, the mSLO has a percent wild-type SLO specific activity of less than about 1.5%, more preferably less than about 0.5%, and most preferably less than about 0.1%, based upon a wild-type SLO specific activity of $4\times10^5$ hemolytic units/mg wild-type SLO. These values are relative; thus, if percent wild-type SLO specific activity is based upon a wild-type SLO specific activity of $1\times10^6$ hemolytic units/mg, the above values are decreased by a factor of 2.5 (i.e., 1.5% becomes 0.6%; 0.5% becomes 0.2%; 0.1% becomes 0.04%).

The preceding is detailed because the "specific activity" of wild-type SLO has been described as being as high as about $1\times10^6$ hemolytic units/mg, although specific activity of about $4\times10^5$ hemolytic units/mg has also been described. Alouf, J. E. "Streptococcal Toxins (Streptolysin O, Streptolysin S, Erythrogenic Toxin)." Pharmac. Ther. II: 661–717 (1980), which is incorporated herein by reference. Accordingly, because the reported "specific activity" of wild type SLO is elusive, the foregoing percentages accomodate this fact.

For convenience, as used herein, the term "vector" means a circular DNA macromolecule comprising at least one restriction site and at least one promoter region. The term "plasmid" means a vector further comprising a portion of a genome of interest, including, inter alia, a gene. The term "host" means a cell capable of being transformed by a plasmid.

As those in the art appreciate, most vectors are selected with respect to a desired outcome. For example, in a commercial setting, high-level expression of the gene of interest will typically be preferred such that vectors with an appropriate promoter conducive to such expression will be chosen; on the other hand, in a research setting, such high level expression may not be critical such that a vector having translational and transcriptional signals that are under the control of regulatory elements of the host may be appropriate. Accordingly, in selecting a vector appropriate for the desired outcome, it is often useful to concurrently focus on the promoter gene of the vector of interest.

Promoter genes which achieve very high levels of mRNA production include, for example, $p_L$, $p_{tac}$, and $p_{T7}$. This list is not intended, nor is it to be construed, as an exhaustive list. Rather these promoters are used as exemplars for purposes of the discussion to follow. Those in the art can readily select an appropriate vector having a desired promoter which can provide equivalent results vis-a-vis the listed promoters.

For example, $p_{T7}$ is used in conjunction with T7 RNA polymerase which synthesizes RNA at a rate several times that of *E. coli* RNA polymerase and which terminates transcription less frequently than *E. coli* RNA polymerase. T7 RNA polymerase is highly selective for initiation at its own promoter sequence; accordingly, it does not initiate transcription from any sequences on *E. coli* DNA. Furthermore, T7 RNA polymerase is resistant to antibiotics such as rifampicin that inhibit *E. coli* RNA polymerase. Therefore, the addition of rifampicin, for example, to cells that are promoting T7 RNA polymerase results in the exclusive expression of genes under the control of a T7 RNA polymerase promoter, i.e., $p_{t7}$.

Expression using the T7 RNA polymerase/$p_{T7}$ system relies upon (typically) a two-plasmid system: the first plasmid comprises the gene to be expressed and $p_{T7}$; the second plasmid comprises the gene for T7 RNA polymerase. The second plasmid, e.g. pGP1-2 (which comprises the gene for T7 RNA poylmerase; see Tabor and Richardson, *Proc.Natl.Acad. Sci. U.S.A.* 82: 1074–1078(1985)), can either permanently reside in *E. coli* or can be introduced into *E. coli* with a specialized phage, such as, e.g., an M13 vector (such as, e.g., mGP1-2, see Tabor and Richardson), or a γ vector (such as, e.g., CE6, see Studier and Moffett, *J.Mol.Biol.*, 189: 113–130(1986)) comprising the T7 RNA polymerase gene.

Typically, the second plasmid comprising the T7 RNA polymerase gene is under the control of a heat inducible *E. coli* promoter, i.e., by raising the temperature from, e.g., 30° C. to 42° C., the heat inducible *E. coli* promoter is switched on, which will in turn switch on the $p_{T7}$ promoter of the first plasmid, thereby leading to the expression of, e.g., the gene of interest. Thus, when using a T7 RNA polymerase/$p_{T7}$ expression system, the *E. coli* system comprises a heat-inducible promoter, such as, for example lambda $P_L$ with a $CI_{857}$ repressor.

Examples of vectors comprising $p_{T7}$ include, e.g., the pT7 series (pT7-5, pT7-6, and pT7-7, which are derivatives of pT7-1; see Tabor and Richardson, supra.) and the pET series (see Studier et al., *Methods Enzymol.* 185:60–89(1990)).

Another vector system comprises a $p_L$ promoter gene. The $p_L$ promoter is derived from the γ bacteriophage and is one of the most powerful regulated *E. coli* promoters. Transcription from $p_L$ can be fully repressed and therefore plasmids comprising $p_L$ can be stabilized by the γ repressor, cI. This repressor is typically supplied by an *E. coli* host which comprises an integrated copy of a portion of the γ genome. Such an *E. coli* host, referred to as an "*E. coli* lysogen" is characterized as follows: (i) it supplies the γ regulatory proteins cI and N (an anti-termination function); and (ii) it does not provide lytic components that would normally lead to cell lysis. Accordingly, *E. coli* lysogens transfected with plasmids comprising, e.g., a gene of interest and $p_L$, can be grown initially to high density without expression of the gene and subsequently induced to synthesize the protein under inactivation of the repressor. Examples of $p_L$ based vectors are described in, e.g., U.S. Pat. No. 4,925,799 ("pAS1"), Shatzman and Rosenberg, "The pAS Vector System and Its Application to Heterologous Gene Expression in *Eschericia coli.*" *Heptalogy* 7:305–355(1987), and Rosenberg et al., "The Use of pKC30 and its Derivatives for Controlled Expression of Genes." *Methods Enzymol* 101: 123–139(1983).

The $p_{tac}$ promoter is a hybrid promoter based on the tac and lac promoters. de Boer, et al. "The tac promoter: A functional hybrid derived from the trp and lac promoters." *Proc.Natl.Acad. Sci.USA* 80:21–25(1983); see also, Amann, et al. "Vectors bearing a hybrid trp-lac promoter useful for regulated expression of cloned genes in *Eschericia coli.*" *Gene* 25:167–178(1983). Because $p_{tac}$ includes the lac operator region, it can be repressed by *E. coli* strains that overproduce the lac repressor, and be fully induced by addition of isopropyl β-D-thiogaloctoside (IPTG) thereto.

All of the foregoing references are incorporated herein by reference.

The choice of an appropriate vector/host system is within the realm of the particular needs of the artisan. A most preferred vector is based upon the $p_L$ promoter. Table I sets forth a representative (not exclusive) list of suitable vectors and hosts, as well as the sources thereof.

TABLE I

| Vector | Host* | Source |
|---|---|---|
| pBTac1 DNA | JM101, JM105, JM107, JM109 | (1) |
| pBTac2 DNA | JM101, JM105, JM107, JM109 | (1) |
| pNH8A | D121OPH, D1210 | (2) |
| pNH16A | D121OPH, D1210 | (2) |
| pNH18A | D121OPH, D1210 | (2) |
| pPROK-1 | JM109 | (3) |
| pEX2 | N4830-1 | (3) |
| pUC19 | JM101, JM105, JM107, JM109 | (4) |
| p33 | AR120, AR58 | (5) |
| pΔ33 | AR120, AR58 | (5) |

TABLE I-continued

| Vector | Host* | Source |
|---|---|---|
| $_pP_L$-Lamda | N99cI$^+$-N4830-1 | (6) |

* = *E. COLI* CELL
(1) = BOEHRINGER MANNHEIM
(2) = STRATAGENE CLONING SYSTEMS
(3) = CLONETECH LABORATORIES, INC.
(4) = BETHESDA RESEARCH LABS
(5) = SMITHKLINE BECKMAN NOW SMITHKLINE BEECHAM
(6) = PHARMACIA LKB

For the following examples, the vectors pΔ33 and pBTac2 DNA were utilized in conjunction with the host strains AR120 and JM105, respectively, for the subcloning (initially from pUC19 vector) and expression of mSLO.3/6.

EXAMPLES

The following Examples directed to preferred embodiments are not intended, nor are they to be construed to be, limitations on the disclosure of the claims to follow.

EXAMPLE 1

Preparation of Partially Digested Genomic Streptolysin O DNA

Genomic DNA was isolated from Streptococcus pyogenes (ATCC #10389) using the technique described in Kehoe, M. et al. *Infect. Immun.,* 55:3228–3232 (1987) (hereinafter "Kehoe, 1987"), which is incorporated herein by reference. Approximately 1 mg of *S. pyogenes* DNA was obtained using this procedure (925 μg).

To 370 μl of *S. pyogenes* DNA (2.5 μg/μl) was added 300 μl of 10X High Salt Buffer (1.0M NaCl; 100mM trishydroxyamino methane-chloride ("TRIS-Cl"), pH7.5; 100mM $MgCl_2$; and 10mMdithriothreotol ("DTT")), 2310 μl of deionized $H_2O$ and 20 μl of Bgl II (BRL, Gaithersburg, Md., Cat. #5213SA), for a final volume of 3000 μl. This mixture was maintained at 37° C. and incubated overnight.

To this incubated mixture was added 3000 μl of Reagent A (250 μl phenol, 250 μl chloroform, 10 μl isoamyl alcohol, 1 μl β-mercapthoethanol). This mixture was agitated prior to centrifugation in order to separate the aqueous and the organic layer. The aqueous supernantant was then precipitated with 0.3M NaOAc and 95% ethanol. The precipitate was then redissolved in 250 μl TE (10mM TRIS-Cl, pH 7.5; 1mM EDTA) and 25 μl of 10X loading dye (0.2M EDTA; 50% glycerol; 0.25% xylene cyanol; 0.25% bromophenol blue) was added thereto, followed by electrophoresis on 1% agarose gel. The Bgl II partially digested *S. pyogenes* genomic DNA fragments were then evaluated according to size.

As noted, SLO has an approximate molecular weight of 65,000 to 70,000 daltons. Each amino acid has an approximate molecular weight of 110 daltons, such that (conservatively estimating) a 70,000 dalton protein would be encoded by approximately 636 codons, or 1909 base pairs. Accordingly, the partially digested fragments of between about 2,000 to 2,500 base pairs (i.e., 2.0 to 2.5 Kb), as determined by the aforementioned gel electrophoresis method, were purified. The purified fragments were then resuspended in 150 μl of TE. For convenience, these are designated herein as "SLO inserts".

EXAMPLE 2

Preparation of Streptolysin O Containing Plasmids

The vector utilized was pUC19 (BRL, Cat. #5364SA) cut with Bam HI (BRL, Cat. #5201SA).

To 1 μl of cut pUC19 vector was added 15 μl of the SLO inserts, 3 μl of 10X ligation buffer (660mM TRIS-Cl, pH 7.5; 50mMmagnesium chloride; 10mM DTT; 10mMATP). A final volume of 30 μl was achieved by the addition of 8 μl of deionized $H_2O$. To this mixture was added 2 μl of T4 ligase (USB, 5 μg/μl); incubation thereof at room temperature proceeded overnight. For convenience, the resulting material is designated as "SLO plasmid candidates".

EXAMPLE 3

Screening of SLO Plasmid Candidates

Host cells *E. coli* strain JM105 were transformed with the SLO plasmid candidates as follows. A vial containing 300 μl of frozen JM105 competent cell was thawed, and 16.0 μl of the SLO plasmid candidates was added thereto. This admixture was incubated on ice for 30 min, followed by heat shock in a 37° C. water bath for 2 min. Thereafter, the transfected JM105 solution was added to 2ml of LB medium (10g Bacto-tryptane; 5g Bacto yeast extract; 10g NaCl; liter deionized water; pH 7.5 with sodium hydroxide), followed by shaking (200RPM) for 30min at 37° C. Plating was thereafter accomplished on LB Ampicillin plates, followed by incubation overnight at 37° C.; for convenience, these are designated "SLO trans formants".

Screening was accomplished utilizing a unique procedure. Following overnight growth, the colonies were overlaid with 3ml of 2.5% washed rabbit red blood cells in 0.8% agarose in PBS/10mM DTT, which was spread to cover the plates. After 40min of incubation at 37° C., colonies comprising SLO were surrounded by small zones of hemolysis. In order to confirm that these colonies comprised SLO, a 25-mer oligonucleotide probe derived from nucleotides 670 through 694, inclusive, of the reported DNA sequence of SLO (see Kehoe, 1987) was used as a probe. The probe was prepared with a BioSearch 8600 DNA synthesizer, and labelled with $^{32}p$ following the T4 polynucleotide kinase procedure described in Maniatis et al., *Molecular Cloning*, CSPL (1982), pp. 122–126 (hereinafter "*Molecular Cloning*").

The blood overlay screening technique proved to be an efficient and accurate method for rapidly screening the SLO expressed by the SLO transformants. Because a property of SLO is the ability thereof to lyse red blood cells, red blood cells from any source can be utilized, i.e., human, mouse, goat, rabbit, etc. Rabbit red blood cells are preferred due to the availability thereof.

An SLO clone that led to the expression of protein which evidenced hemolytic activity and which hybridized with the 25-mer probe was designated "pUC19-SLO-B". For convenience, the non-vector DNA sequence thereof is designated herein as "rSLO-candidates".

EXAMPLE 4

Optimization of Expression and Determination of Solubility

In order to optimize the expression of rSLO-candidates, timed-digestion of rSLO-candidates using Bal-31 was accomplished. Additionally, and as previously noted, solubility of the expressed protein ab initio, i.e., without further chemical modification once expressed, is of import. This is because non-soluble SLO is by definition inactive. Accordingly, an anlysis was also made to determine if the exprersed protein was soluble, i.e. was located in a supernatant as opposed to a pellet, following centrifugation.

The pUC19-SLO-B was initially cut with BstE II (New England Bio Labs, Cat. #162, 10 U/μl) as follows. To 20 μl of pUC19-SLO-B (2.5 μg/μl) was added 40 μl of 10X High Salt Buffer, 335 μl deionized $H_2O$, and 5 μl of BstE II. This admixture was incubated at 60° C. for 2 hrs, followed by extraction with 400 μl of Reagent A, and precipitation with 44 μl of 3M NaOAc (pH 4.8) in 888 μl of 95% ethanol. The precipitant was then redissolved in 40 μl $H_2O$. Thereafter, 90 μl of $H_2O$, 20 μl of 10X Bal-31 Buffer (120mM $CaCl_2$; 120mM$MgCl_2$, 2.0M NaCl; 0.2M TRIS-Cl, pH 8.0; 10mM EDTA), and 50 μl of 1 mg/ml Bovine Serum Albumin, was admixed with the redissolved precipitant. This was followed by the addition-of 10 μl of Bal-31 (New England Bio Labs, Cat. #213, 100 U/ml), for a total of 210 μl, followed by incubation at room temperature. To control the effects of Bal-31, 30 μl aliquots of the 210 μl total solution was removed at 30, 45, 60, 80, 105, 130 and 160 min post-Bal-31 addition, and these aliquots were each admixed in 3.3 μl of 0.2M EGTA, followed by storage on ice. After preparation and storage of the last aliquot, all seven aliquots were pooled, extracted with 230 μl of Reagent A, and precipitated with 23 μl of 3M NaOAc in 506 μl of 95% ethanol. The precipitate was then redissolved in 75 μl of $H_2O$.

A fill-in reaction followed by the addition of 5 μl of 2.5mM dXTP, 10 μl of 10X Medium Salt Buffer (500mM NaCl; 100mM TRIS-Cl, pH 7.5; 100mM$MgCl_2$; 10mMDTT), and 10 μl of 100mM of DTT to 75 μl of the redissolved precipitant, followed by the addition thereto of 6μl of Klenow polymerase (5 U/μl ), and incubation at room temperature for 4 hrs. This admixture was extracted with 100 μl of Reagent A, precipitation with 11 μl of 3M NaOAc in 22 μl of 100% ethanol, and resuspension of the precipitate in 40 μl of $H_2O$.

Following the fill-in reaction, 17 μl of the resuspended precipitate was admixed with 3 μl of a linker comprising a Bam HI sequence (New England Bio Labs, Cat 1021) and 5 μl of 5X linker ligation buffer (250mMTRIS-Cl, pH 7.6; 50mM$MgCl_2$; 5mMDTT; 5mMATP; 2.5% (w/v) PEG 8000 (J. T. Baker, Cat. #U222-09)). This was followed by the addition thereto of 2 μl of T4 ligase (5 U/μl), and incubation thereof for 6hrs at room temperature. For convenience, the resulting material is referred to as "ca/ew".

*E. coli* strain JM105 was transformed with ca/ew as described above, followed by overnight growth as described above in Example 3. To determine if the plasmids comprised the Bam HI linker, to 40 μl of ca/ew (0.5 μl g/μl ) was added 40 μl of 10X Medium Salt Buffer, and 320 μl deionized $H_2O$. To this mixture was added 5 μl EcoRI (BRL, Cat #5202 SA, 10U/μl ), followed by incubation at 37° C. for 2 hrs. In order to ensure that the plasmid was cut, gel electrophoresis (1% agarose gel) was conducted; this resulted in a smear of different sizes, indicating a successful cut. To the cut plasmid was added 8 μl of 5M NaCl, followed by 5 μl of Bam HI (10 U/μl ). This mixture was incubated for 37° C. for 2hrs. Determination of the size of the rSLO-candidate sequence subjected to Bal-31 digestion was conducted by gel electrophoresis (1% agarose gel). This resulted in a band of interest at about 1.2 to about 2.0 Kb which comprised rSLO-candidates. Thus, the initial fragments of 2.0 to 2.5 Kb which evidenced hemolytic activity had been significantly decreased in size.

The band which comprised rSLO-candidate was cut from the gel and purified in 15 μl of TE such that rSLO-candidate was available for ligation in pUC19 vector previously cut with Bam HI and ECoRI. In order to accomplish such ligation, 10 μl of the gel-purified rSLO candidate was admixed with 4 μl of the previously prepared vector, 2 μl of 10X ligation buffer, 2 μl of 10mMATP, and 2 μl of deionized $H_2O$. To this admixture was then added 2 μl of T4 ligase, followed by incubation at room temperature for 6 hrs. *E. coli* host cell strain JM105 was transformed by these plasmids as above, and active colonies were screened by the red-blood cell overlay method disclosed above. Active colonies were then selected, innoculated in LB Medium/100 μg/ml Ampicillin and grown overnight under the conditions described above.

Following overnight growth, the cells were centrifuged for 5min at 8000RPM at 4° C., and the resulting pellet resuspended in 2ml of Reagent B (150mMNaCl; 20mM TRIS, pH 7.0; 1mM EDTA). Thereafter, the resuspended cells were subjected to sonication for 2X 30sec. on ice, followed by centrifugation at 9500RPM for 40min at 4° C. using a Beckman JA20.1 centrifuge to obtain the expressed protein.

At this stage, if the rSLO-candidate led to the expression of a soluble protein, that protein would be located in the supernatant. Accordingly, analysis was conducted for the presence of rSLO-candidate in the supernatant using standard Western blot protocols for determination of an antigenically active protein. The results of such Western blot analysis indicated that there was an SLO fusion product in the supernatant which was recognized by horse anti-SLO antibodies. One such fusion product was selected and designated "rSLO.3" For convenience, the DNA sequence leading to the expression of rSLO.3 is also referred to as rSLO.3. High level expression of rSLO.3 was thereafter attempted.

EXAMPLE 5

High Level Expression of rSLO.3

Removal of rSLO.3 from the plasmid comprising pUC19 vector was effectuated as follows. To 15 μl of the plasmid comprising rSLO.3 (0.5 μg/μl) was added to 40 μl of 10X Sma I Buffer (200mM KC1; 100mM TRIS-Cl, pH 8.0; 100mM $MgCL_2$; 10mMDTT), and 345 μl of deionized $H_20$. To this mixture was added 5 μl l Sma I (BRL, Cat #5228 SA, 10U/μl), followed by incubation at 37° C. for 2hrs. In order to ensure that the plasmid was cut, gel electrophoresis (1% agarose gel) was conducted; this resulted in a single band, indicating a successful cut. To the cut plasmid was added 8 μl of 5M NaCl, followed by 5 μl l of Bam HI (10U/μl). This mixture was incubated for 37° C. for 2 hrs. To ensure that the rSLO.3 sequence was successfully cut from the approximately 2.7Kb pUC 19 vector, gel electrophoresis (1% agarose gel) was conducted. This resulted in two bands, one at about 2.7Kb (the vector), and the other at about 1.4Kb (rSLO.3). This band was cut from the gel and purified in 15 μl of deionized $H_2O$ such that rSLO.3 was available for ligation in pΔ33 vector previously cut with Bam HI and Sma I.

To 2 μl of above-derived rSLO.3 DNA was added 2 μl of the above described vector, 1.5 μl l of 10X ligation buffer, 1.5 μl of 10mMATP, and 8 μl of deionized $H_2O$. To this admixture was added 2 μl of T4 ligase (10 U/μl ), followed by incubation for 5 hrs at room temperature. Such incubation resulted in plasmids comprising rSLO.3 and pΔ33 vector.

*E. coli* strain AR120 was transformed with the above-described plasmids in accordance with the procedure outlined for *E. coli* strain JM105. Thereafter, a DNA mini prep described in *Current Protocols in Molecular Biology*, Auschel, F. M. et al., Eds, John Wiley & Sons (New York) (1987), Section 1.6., followed by cutting the plasmids with Bam HI and Sal I (BRL, Cat. #5217 SA) to determine if the plasmids comprised rSLO.3. Those host cells transformed with plasmids comprising rSLO.3 were then subjected to induction via the nalidixic acid protocol. See Mott, J. E. et al "Maximizing gene expression from plasmid vectors containing the $\gamma p_L$ promoter: Strategies for overproducing transcription termination factor p." *PNAS USA*, 82: 88–92(1985), which is incorporated herein by reference. As those in the art appreciate, nalidixic acid, which damages DNA, induces recA protein, a recovery protein for *E. coli.* A derivative benefit vis-a-vis overexpression is that recA has protease activity, which, inter alia, leads to inactivation of $\gamma cI^+$ repressor; this inactivation leads to overexpression by the $p_L$ promoter.

Specifically, colonies comprising the transformed AR120 were lifted from the agar plates and innoculated in Superboth (Base—129 tryptone, 249 yeast extract, 5 ml glycerol, 900ml distilled $H_2O$; Salt (per liter of base) 1.7 g $KH_2PO_4$, 15.89 $K_2HPO_4$ (anhydrous) 100ml distilled $H_2O$) plus 100 μg/ml ampicillin at 37° C. until the optical density of the medium at $A_{650}$ equalled 0.4. Thereafter, nalidixic acid was added to the innoculated mixture at a final concentration of 60 μg/ml and incubated at 37° C. for 4 hrs. Western blot analysis of the supernatant demonstrated the presence of rSLO.3.

EXAMPLE 6

Mutation of rSLO.3

As those in the art appreciate, organisms are equipped with elaborate mechanisms that keep DNA mutation rates low, from a statistical point of view. There are at least three steps required to prevent mutations from occurring during DNA replication: (i) selection of a nucleotide complementary to the template (i.e. the DNA macromolecule being replicated) by DNA polymerase (an enzyme which catalyzes the addition of a nucleotide to the 3′ end of a DNA chain); (ii) removal of a noncomplementary base by an "editing nuclease" (i.e., an enzyme capable of degrading, e.g., a nucleotide); and (iii) correction of a misincorporated nucleotide.

As is further appreciated by the skilled artisan, "murators" are a special class of mutations that render various genes unstable. Bacteria mutator strains, for example, *E. coli* mutator strains, have been utilized to investigate the mechanisms by which organisms control their mutation rates. Accordingly, identification of specific genes within a strain of,.e.g., *E. coli,* having mutations, allows for investigation of mutator activity.

The dam, mutS, mutR, mutL, and uvrD genes are involved in the process of mismatch repair; accordingly, *E. coli* strains which include defective versions of these genes exhibit moderately high mutator activity. Some *E. coli* mutator genes cause specific changes in the DNA sequence being replicated. For example, the mutS3 mutator strain of *E. coli* produces bi-directional transitions and is apparently sensitive to base sequence, in that it mutates one A:T base pair but does not mutate a second A:T base pair located less than 50 nucleotides away. The mutt mutator strain of *E. coli* is unique in displaying a strict specificity, i.e., only A:T→C:G transitions are induced. The mutD mutator strain of *E. coli* is also notable because it results in mutation frequencies of $10^3$ to $10^5$ times that of wild-type *E. coli*. Transversions of A:T←→G:T, transitions of A:T←→T:A, and A:T→C:G substitutions are associated with the mutD strain. While the tendencies of certain mutator strains are known, predicting exactly when or where along the DNA macromolecule a mutation will take place cannot be reasonably predicted.

In an effort to effectuate a mutation of rSLO.3 (having as a desired objective obtaining a mutated form thereof), the *E. coli* mutator strains mut D and mutt were utilized. A most preferred mutator strain is mutD. Vials containing 300 μl each of frozen competent cell mutD and mutt strains were thawed, and 1 μl of the plasmids from Example 4 was added thereto. This admixture was incubated on ice for 30 min., followed by heat shock in a 37° C. water bath for 2 min. Thereafter, the transformed mutD and mutt host cells were added to 2 ml of LB medium, followed by shaking (200RPM) for 30 min. at 37° C. Innoculation was accomplished as follows: to the incubated mixture was added 10 ml of LB Medium/100 μg/ml Ampicillin, followed by overnight growth at 37° C. Innoculation was repeated 5 (five) times, followed by the DNA mini-prep procedure referenced above. This resulted in plasmids comprising rSLO.3 mutation sequence candidates.

*E. coli* strain JM105 was thereafter transformed with these plasmids as described above, followed by plating and overnight growth as described above. Screening was accomplished using the unique blood-overlay protocol disclosed above. Most of the resulting colonies were active (i.e. non-mutants); however, a few of the resulting colonies did not lead to lyses of the red blood cells; these are referred to herein as mSLO-candidates. The colonies comprising mSLO-candidates were picked for determination of the immuno-activity thereof. This was accomplished using standard Western blot protocols (horse AS0). One of the mSLO-candidates which evidenced immunoactivity with horse ASO was selected for high level expression.

EXAMPLE 6

High Level Expression of mSLO

Having cloned a gene for mSLO, high level expression thereof using a $p_L$ based vector was accomplished. The vector was pΔ33; the *E. coli* host strain was AR120.

Removal of mSLO from the plasmid comprising pUC19 vector was effectuated as follows. To 15 μl of the plasmid comprising mSLO (0.5 μg/μl ) was added 40 μl of 10X Sma I Buffer, and 345 μl of deionized $H_2O$. To this mixture was added 5 μl 1 Sma I, followed by incubation at 37° C. for 2hrs. In order to ensure that the plasmid was cut, gel electrophoresis (1% agarose gel) was conducted; this resulted in a single band, indicating a successful cut. To the cut plasmid was added 8 μl 1 of 5M NaCl, followed by 5 μl of Bam HI (10U/μl ). This mixture was incubated for 37° C. for 2hrs. To ensure that the mSLO sequence was successfully cut from the approximately 2.7Kb pUC 19 vector, gel electrophoresis (1% agarose gel) was conducted. This resulted in two bands, one at about 2.7Kb (the vector), and the other at about 1.4 Kb. The DNA of within this band is referred to herein as "mSLO.3/6" and protein expressed by this DNA is also referred to as mSLO.3/6. This band was cut from the gel and purified in 15 μl of deionized $H_2O$ such that mSLO.3/6 was available for ligation in pΔ33 vector previously cut with Bam HI and Sma I.

To 2 μl of above-derived mSLO.3/6 was added 2 μl of the above described vector, 1.5 μl of 10X ligation buffer, 1.5 μl of 10mMATP, and 8 μl of deionized $H_2O$. To this admixture was added 2 μl of T4 ligase (10 U/μl ), followed by incubation for 5 hrs at room temperature. Such incubation resulted in plasmids comprising mSLO.3/6 and pΔ33 vector.

*E. coli* strain AR120 was transformed With the above-described plasmids in accordance with the procedure outlined for *E. coli* strain JM105. Thereafter, a DNA mini prep as referenced above was performed, followed by cutting the plasmids with Bam HI and Sal I (BRL, Cat. #5217 SA) to determine if the plasmids comprised mSLO.3/6. Those host cells transformed with plasmids comprising mSLO.3/6 were then subjected to the nalidixic acid and innoculation protocols described above. As with rSLO.3, Western blot analysis of the supernatant demonstrated the presence of mSLO.3/6.

EXAMPLE 8

Specific Activity of mSLO.3/6

Protein concentration and specific activity of non-purified mSLO.3/6 obtained from Example 7 was determined and compared with the protein concentration and specific activity of non-purified rSLO.3 immediately following nalidixic acid induction of each.

Protein concentrations for both the rSLO.3 and mSLO.3/6 crude extracts were derived using the BioRad Protein Assay method (Coomassie Blue G-250). Nalidixic acid induced proteins mixtures were centrifuged at 8000RPM for 5min at 4° C. and the pellets resuspended in 500 μl sonication buffer (40mM TRIS, pH 7.5; 1 mM EDTA; lmM DTT; 200 mMNaCl). The resuspended pellets were then sonicated for 2X 30sec on ice, followed by centrifugation at 12,000 RPM for 40min at 4° C. Thereafter, 5 μl of the resuspended rSLO.3 and mSLO.3/6 mixtures were analyzed for protein concentration (OD reading at $A_{595}$), and the protein concentration of each was determined to be 4.6 μg/μl. Western blot analysis was conducted for each sample; the gel pattens for 0.2, 2, and 10 μg of each protein were identical, as is evident from FIG. 5.

Specific activity comparisons were determined by serial dilutions of the above described crude extracts and addition thereto of washed rabbit red blood cells ("RRBC"), followed by spectrophotometric reading (OD reading at $A_{541}$). 5ml of fresh rabbit blood was washed 2X with 45 ml of PBS including 10mM DTT, followed by centrifugation at 2000 RPM for 5min at 4° C. Thereafter, 1.125 ml of the washed rabbit red blood cells ("RRBC") were drawn from the bottom of the tube and 48.8751 ml of PBS/10mM DTT was added thereto. This resulted in a solution comprising 2.25% RRBC. For the hemolytic assays, 500 μl of the 2.25% RRBC was added to 500 μl of 1:2 serially diluted rSLO.3 and mSL0.3/6 in PBS/10mM DTT, followed by incubation at 37° for 30min.

These serial dilutions were spectrophotometrically analyzed (OD readings at $A_{541}$). This analysis indicated that 0.2 μl of the diluted rSLO.3 crude extract caused 50% hemolysis of the RRBC; 0.2 μl of the diluted extract is equivalent to 2 μl of the culture itself. Accordingly, the rSLO.3 crude extract evidenced one hemolytic unit ("HU") per two microliters, or 500 HU/ml. The mSLO.3/6 crude extract had substantially no hemolytic activity, i.e, 100 μl of the resuspended mSLO.3/6 culture caused less than 6% hemolysis of the RRBC, or 0.2 HU/ml. Accordingly, there is 2,700 times less hemolytic activity associated with mSLO.3/6 compared to rSLO.3.

As noted, the protein concentration of the crude extracts was determined to be 4.6mg/ml. Accordingly, the specific activity of rSLO.3 derived from the pΔ33-AR120 expression system was 108.7HU/mg, while the specific hemolytic activity of mSLO.3/6 derived from this system was 0.04HU/mg. It is noted that because these are values for a crude (i.e. non-purified) extract, these values are predicated upon total protein concentration of the extract. For a purified extract, the specific activity values increase.

The DNA and amino acid sequences of mSLO.3/6 was thereafter determined (Lark Sequencing Technologies, Houston, Tex.), and are presented in FIGS. 1 and 2, respectively. In FIG. 1, the first codon (ATG) was donated by the pΔ33 vector, and the second codon (GAT) was from the Bam H1 linker. For comparative purposes, the DNA and amino acid sequencing of rSLO.3 are presented in FIGS. 3 and 4.

There is a single codon difference between the sequences of rSLO.3 and m SL0.3/6 at codom 487. In rSLO.3, this codon is GAA (GLU amino acid) while in mSLO.3/6, this codon is AAA((Lys amino acid).

EXAMPLE 9

Recovery of mSLO.3/6

The following procedure is for approximately 200 grams of transformed host cells (i.e., approximately 6 grams total protein).

Transfected host cells were resuspended in 200 mls of Reagent C. (40mM TRIS, pH 7.5; lmM EDTA; 0.1% 2-mercaptoethanol), followed by the addition of 100mM PMSF. Thereafter, the cells were disrupted by sonication, followed by the addition of 4 ml of 100mM PMSF. This admixture was centrifuged for 30 min at 4° C. at 15,000 RPM.

The resulting supernatant was removed and saved; 200 ml of Reagent C. was added to the pellet, followed by the addition of 4 mls of 100mM PMSF. The resuspended pellet was then sonicated, followed by centrifugation as above. The resulting supernatant was then removed and pooled with the previous supernatant, and the pH thereof was adjusted to 7.0 with NaOH.

To the final volume of supernatant was slowly added (with stirring at room temperature) Polymin P (Aldrich Chemicals) to a final concentration of 0.75%. This admixture was then centrifuged for 30 min at room temperature at 10,000 RPM, followed by retrieval of the supernatant. Solid sodium sulfate was slowly added with stirring to 80% saturation of the supernatant.

Thereafter, the admixture was stirred for 2hrs at 4° C., followed by centrigation for 30min at 4° C. at 15,000 RPM. The pellet was then retrieved and resuspended in 400mls of saturated ammonium sulfate, pH 7.0. The admixture was then centrifuged for 30min at 4° C. at 10,000 RPM, followed by retrieval of the pellet and resuspension thereof in 200 mls in Reagent D (20mM TRIS, pH 7; 1 mM EDTA; 0.1% 2-mercaptoethanol).

The resuspended pellet was then dialyzed against 2 liters of Reagent D, with 4 changes, at 4° C. Sufficient room was left in the dialysis bag in that the volume of the sample increases. Following dialysis, the pH of the sample was checked, and adjusted to 7.0 with NaOH.

The sample was then loaded onto a Pharmacia Fast Flow S-Sepharose column equilibrated in Reagent D. A 400 ml bed volume was found to be sufficient to remove the mSLO.3/6 from the sample. The flow through, comprising *E. coli* proteins, was collected and discarded, and the column was washed with approximately 1 liter of Reagent D.

The mSLO.3/6 was eluted with 2×1 liter 0.0 to 0.4M NaCl gradient in Buffer B. The fractions were analyzed by SDS acrylamide gel (9%), and fractions with high amounts of mSLO.3/6 were pooled. Approximately 250ml of pooled mSLO.3/6 was recovered.

Using the above procedure, approximately 60% of the original total protein (i.e. approximately 0.36 grams) was mSLO.3/6, which can be stored at 4° C. until needed.

EXAMPLE 10

Purification of mSLO.3/6

Purification of mSLO.3/6 was accomplished to a purity of at least 80% using the following protocol.

Approximately 600g of frozen cell paste derived in accordance with the protocol described in Example 9 was thawed (37° C.), resuspended in 3 liters of cold lysis buffer (40mM TRIS-C1, pH 7.0; 1 mm EDTA; 0.1% 2 -mercaptoethanol; 2M Nact; 4° C.) and sonicated for 60 min at 4° -10° C. with a Heat Systems Ultrasonics Continuous Flow sonicator (Farmingdale, N.Y., No. W-385). Thereafter, the material was centrifuged on a Beckman JA10 centrifuge at 9500 RPM for 40 min at 20° to 26° C. Approximately 3 liters of supernatant was retrieved.

To the supernatant was added at 12.5% stock solution of Polymin P precipitant (Aldrich, Milwaukee, Wis.) to a final concentration of between 0.2 to 0.3%. The solution was then stirred for 1 hr at room temperature and the precipitate discarded. The pH of the liquid portion was then adjusted to 7.0 with NaOH. This liquid was then permitted to stand overnight at room temperature.

Thereafter, the solution was centrifuged as above, and a clear supernatant retrieved. The supernatant was then loaded onto a 1 liter phenyl-sepharose HIC column (Pharmacia, Piscataway, N.J.) at 2 ml/min. at room temperature. Thereafter, the column was washed with an elution buffer (20mM TRIS-Cl, pH 7.0; 1mM EDTA; 0.1% BME) at 7ml/min. Fractions were monitored by SDS-PAGE electrophoresis using the Pharmacia Phast-Page™ System. Protein concentration was determined with the BioRad Protein Assay Kit. Fractions containing protein were then pooled.

The pooled fractions was then loaded onto a 1 liter Blue Affinity Column (BioRad, Richmond, California) at 2 ml/mm at room temperature, followed by washing using the elution buffer described above at 2 ml/min. at room temperature for two column volumes.

Elution of bound protein was accomplished using an NaCL density gradient of 0.0 to 0.8M, pH 7.0. Fractions were monitored with the Phast-PAGE System and protein concentration determined with the BioRad Protein Assay Kit. A single peak was obtained at 0.3–0.4M on the NaCL density gradient. Purity of the eluted mSL0.3/6 was evaluated using a Beckman DU 7500 spectrophotometer, based upon analysis of major band homogeneity obtained from gel electrophoresis (12% SDS-polyacrylamide) of six different amounts of the eluted mSLO.3/6 (16, 8, 4, 2, 1, 0.5 μg mSLO.3/6). The evaluated purity of mSLO.3/6 (and rSL0.3 for comparative purposes) based upon major band homogeneity is set forth in Table 2:

TABLE 2

| mSLO.3/6 and rSLO.3 (μg) | Percent Homogeneity | |
|---|---|---|
| | mSLO.3/6 | rSLO.3 |
| 0.5 | >99.0% | >99.0% |
| 1.0 | >99.0% | >99.0% |
| 2.0 | >99.0% | 94.4% |
| 4.0 | 86.8% | 82.4% |
| 8.0 | 85.1% | 81.4% |
| 16.0 | 81.9% | 80.1% |

Figure 6A:
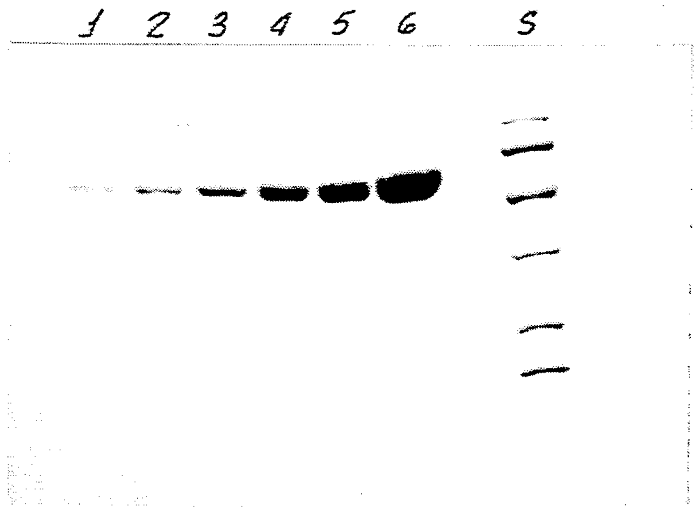
FIG. 6(A) is the result of gel electrophoresis of purified mSLO.3/6
Figure 6B:
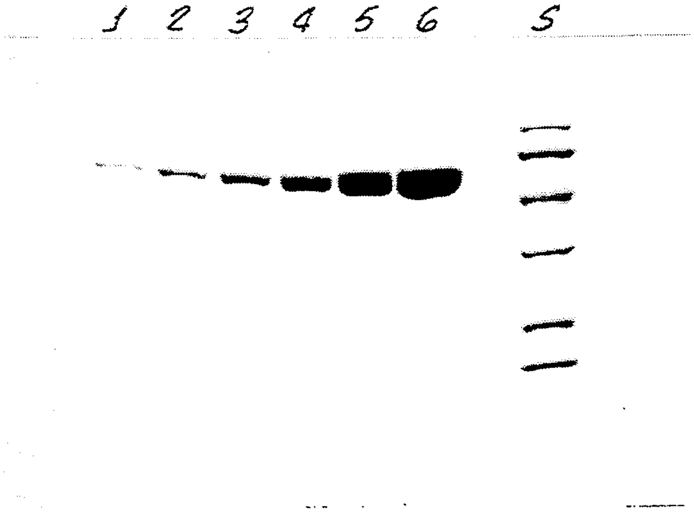
FIG. 6(B) is the result of electrophoresis of and rSLO.3.

The gel electrophoresis results are presented in FIG. 6 where A is mSLO.3/6 and B is rSLO.3.

EXAMPLE 11

Specifc Hemolytic Activity (Titer) of Purified mSLO.3/6

Figure 7:
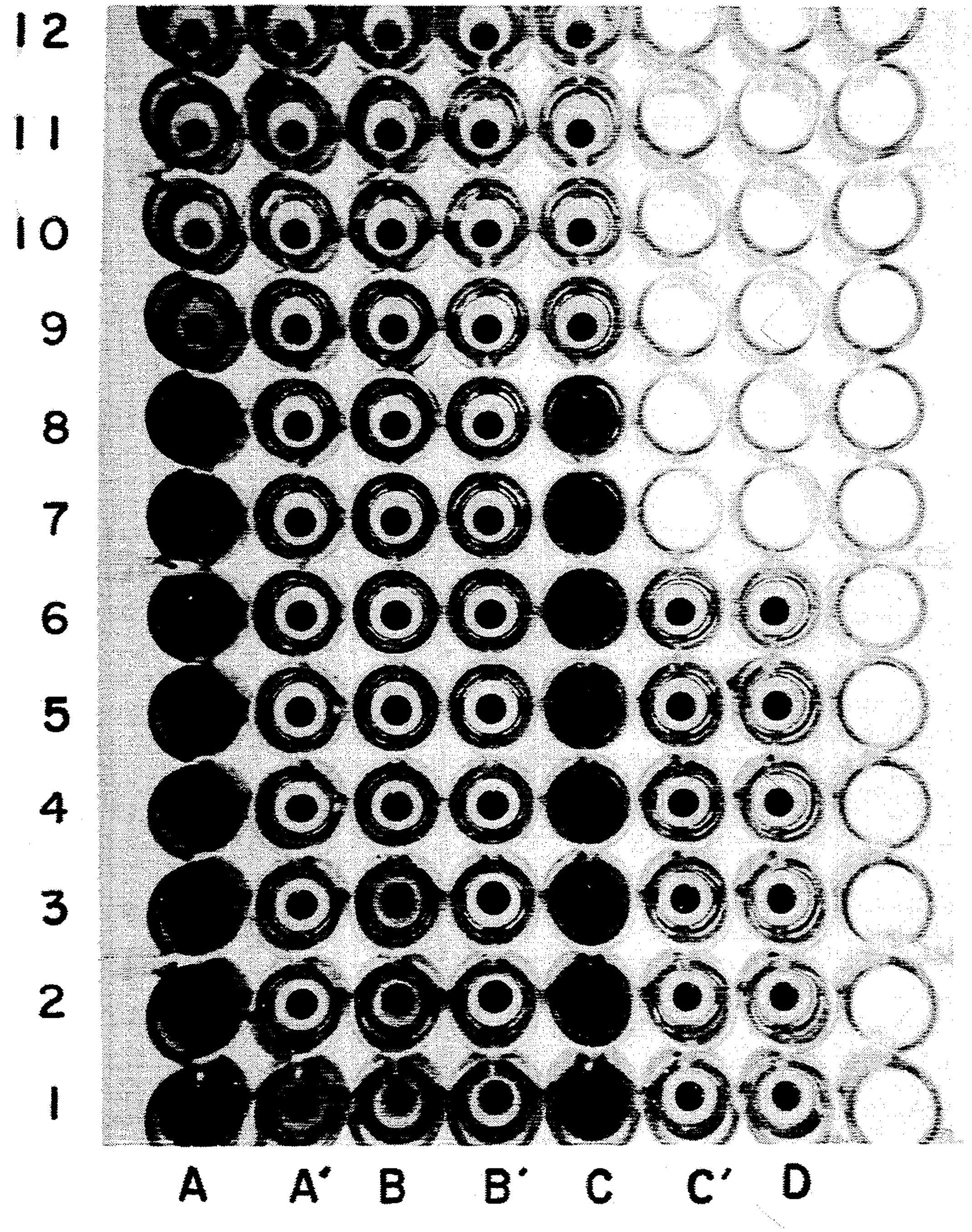
FIG. 7 is the results of titer experiments for hemolytic activity of mSLO.3/6, rS10.3 and commercially available SLO.
Figure 8:
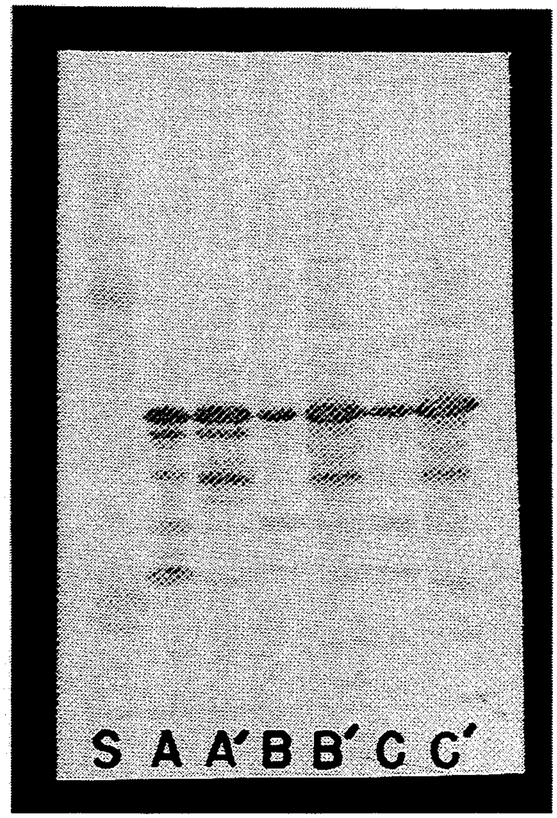
FIG. 8 is the result of Western blot analysis of rSLO.3 and mSLO.3/6 in different vectors.

FIG. 7 provides a photograph of a 96-well microtiter plate. The microtiter wells evidence the results of an analysis of the hemolytic activity (by titer) of rSLO.3; a commercially available wild-type version of SLO (Sigma, Product No. S-5265); and mSLO.3/6.

For the hemolytic assay titers, 0,154g DTT was added to 1 titer of PBS. Fresh rabbit red blood cells (2.5%) were washed with PBS, followed by centrifugation at 2000 RPM for 20min at 4° C.; this protocol was followed three times. Initial dilution of samples was 1:50 in the aforementioned PBS-DTT solution based upon 500 μl PBS-DTT solution to 10 μl of the sample; a 1:2 dilution series was followed for 12 dilutions.

Referencing FIG. 7, in well A1, 200 μl of diluted rSLO.3 was added thereto; in B1, 200 μl of diluted mSLO.3/6; in C1, 200 μl of diluted Sigma SLO. In the remaining wells, 100 μl of PBS-DTT solution was added thereto. Thereafter, 100 μl of the solution from A1 was pipetted into A2; this procedure was repeated such that each well had 100 μl of solution mixture. Thereafter, using an 8 channel pipettor, 100 μl of the washed rabbit red blood cells were added to each well, followed by gently shaking and incubatim at room temperature for 20 minutes. Thereafter, the plate was centrifuged at 500 RPM in a Beckman J4.2 centrifuge for 5 min at 4° C.

Dilutions were as follows as represented in Table 3 for the microtiter wells shown in FIG. 7:

TABLE 3

| | A | A' |
|---|---|---|
| 12 | .24 | $6.0 \times 10^{-5}$ |
| 11 | .49 | $1.2 \times 10^{-4}$ |
| 10 | 1.0 | $2.4 \times 10^{-4}$ |
| 9 | 2.0 | $4.8 \times 10^{-4}$ |
| 8 | 3.9 | $9.5 \times 10^{-4}$ |
| 7 | 7.8 | $1.9 \times 10^{-3}$ |
| 6 | 15.6 | $3.8 \times 10^{-3}$ |
| 5 | 31.3 | $7.6 \times 10^{-3}$ |
| 4 | 62.5 | .015 |
| 3 | 125 | .03 |
| 2 | 250 | .06 |

TABLE 3-continued

| | A | A' |
|---|---|---|
| 1 | 500 | .125 |

Units: μl/ml

In FIG. 7, A,A' is rSLO.3, B,B' is mSL0.3/6, C,C' is Sigma SLO, and D is a negative control (no SLO). Dilutions for B,B, C,C' and D were identical to A,A' except that Sigma SLO was not diluted beyond $1.0\times10^{-3}$ μl /ml and the negative control did not extend past D6.

Plates were read by determining which well in the dilution range did not evidence lysis of the red blood cells. If lysis occurs, then the well is red; the lack of lysis is indicated by the pellet of red blood cells located at the bottom of each well (i.e. the "center" of each well).

As is evident from FIG. 7, no lysis occurred at any titer for mSLO.3/6, while lysis occurred at approximately the same titer for both rSLO.3 and Sigma SLO. Accordingly, mSLO.3/6 evidences substantially no hemolytic activity at any equivalent titer of either the commercially available SLO or rSLO.3.

For determination of hemolytic activity, the concentration of purified mSLO.3/6 was determined (1.2 mg/ml). A 1:16.7 titer of mSLO.3/6 was required to obtain greater than 50% lysis of 2.5% RRBC. Accordingly, the specific hemolytic activity of purified mSLO.3/6 is 14HU/mg (16.7÷1.2). For comparative purposes, the hemolytic activity of rSLO.3 was similarly determined. A 1:25,600 titer of a 0.7 mg/ml concentration of purified rSLO.3 was required to obtain greater than 50% lysis of 2.5% RRBC. Accordingly, the specific hemolytic activity of purified rSLO.3 is $3.6\times10^{4}$HU/mg. This evidences a 2,600 fold difference in specific activity which correlates with the 2,700 fold difference obtained from the crude (non-purified) extracts of Example 8.

EXAMPLE 12

Subcloning of mSLO.3/6

Having obtained, verified and sequenced mSLO.3/6, subcloning and expression thereof using another expression/vector system was initiated. The vector, pBTac 2 DNA (Boehringer Mannheim, Cat. No. 1081381, 10 μg) was cut with Hind III (BRL, Cat. No. 52075A, 10 U/ml) by admixing 30 μl of pBTac2 DNA (1μg/μl), 30 μl of 10X Medium Salt Buffer, 240 μl deionized $H_2O$, followed by addition thereto of 5 μl of Hind III (BRL, Cat. #5207 SA, 10U/μl). This admixture was incubated for 2 hrs at 37° C. Thereafter, the admixture was analyzed by agarose electrophoresis (1% agarose gel) to determine if the vector had been successfully cut; a single band indicated that the cut had been successful.

To the 305 μl admixture was added 300 μl of Reagent A. This admixture was then centrifuged for 5 min at 12,000 RPM on a Beckman microcentrifuge, followed by retrieval of the upper liquid layer. To this liquid layer was added 33 μl of 3M NaOAc (pH 4.8) and 660 μl of ethanol, followed by precipitation overnight at −20° C. This was followed by centrifugation for 10min at 12,000 RPM on a Beckman microcentrifuge. The pellet was retrieved and dried by air. The dried pellet was then resuspended in 150 μl of deionized water.

In order to blunt (fill-in) one end of the Hind III cut vector, the 150 μl solution comprising the resuspended pellet was admixed with 10 μl of 20X dNTP (2.5mM), 20 $\mu$l of 10X MSB and 20 $\mu$l of 100mM DTT. This was followed by the addition of 4 $\mu$l of Klenow polymerase (New England Biolabs, Cat. No. 210, 5 U/ml) and incubation at room temperature for 7 hrs. Thereafter, 300 $\mu$l of Reagent A was added to the incubated mixture, followed by centrifugation for 5 min at 12,000 RPM. The upper liquid layer was retrieved and precipitated as above. The dried pellet was then resuspended in 30 $\mu$l of deionized $H_2O$. For convenience, the filled-in, Hind III cut vector is referred to as "vec.rb".

Thereafter, vec.rb was cut with Bam HI (BRL, Cat No. 5201 SA, 10 U/$\mu$l ). To 30 $\mu$l of vec.rb was added 30 $\mu$l of 10X High Salt Buffer and 240 $\mu$l of deionized $H_2O$. To this admixture was added 5 $\mu$l of Bam HI, followed by incubation for 2 hrs at 37° C. To the incubated mixture was added 300 $\mu$l of Reagent A, followed by centrifugation as above. The upper liquid layer was retrieved and precipitated as above. The dried pellet was then resuspended in 20 $\mu$l of deionized $H_2O$. The resuspended pellet comprised Hind III cut, filledin, Bam HI cut pBTac2 DNA.

The mSLO.3/6 removed from the plasmid described above as follows. To 40 $\mu$l of the plasmid comprising mSLO.3/6 (1 $\mu$g/1 $\mu$l ) was added 10X SmaI Buffer, and 320 $\mu$l deionized $H_2O$. To this mixture was added 5 $\mu$l Sma I (10U/$\mu$l ), followed by incubation at 37° C. for 2 hrs. In order to ensure that the plasmid was cut, gel electrophoresis (1% agarose gel) was conducted; this resulted in a single band, indicating a successful cut. To the cut plasmid was added 8 $\mu$l of 5M NaCl, followed by 5 $\mu$l of Bam HI (10 U/$\mu$l ). This mixture was incubated for 37° C. for 2 hrs. To ensure that the mSLO.3/6 sequence was successfully cut from the approximately 6.3Kb p$\Delta$33 vector, gel electrophoresis (1% agarose gel) was conducted. This resulted in two bands, one at about 6.3Kb (the vector), and the other at about 1.4kB (mSLO.3/6). The 1.4Kb band was cut from the gel and purified in 20$\mu$l of deionized $H_2O$ such that mSLO.3/6 was available for ligation in the prepared pBTac2 vector.

To 3 $\mu$l of the vector was added 2 $\mu$l of mSLO.3/6, 1.5 $\mu$l of 10X Ligation Buffer (0.66M TRIS-Cl (pH 7.5), 50mM$MgCl_2$, 50mM DTT, 10mMATP), 1.5 $\mu$l of 10mMATP and 7 $\mu$l of deionized $H_2O$. Thereafter, 1.5 $\mu$l of T4 Ligase was added thereto, followed by incubation overnight at room temperature. For convenience, this mixture is referred to as the "subclone$_m$".

*E. coli* strain JM105 was transformed with subclone$_m$ as follows. A vial containing 300 $\mu$l of frozen JM105 competent cell was thawed, and 8.0 $\mu$l of subclone$_m$ was added thereto. This admixture was incubated on ice for 30 min, followed by heat shock in a 37° C. water bath for 2 min. Thereafter, the transfected JM105 solution was added to 2 ml of LB medium (10 g Bacto-tryptane; 5 g Bacto yeast extract; 10 g NaCl; 1l deionized water; pH 7.5 with sodium hydroxide), followed by shaking (200 RPM) for 30 min at 37° C. Plating was thereafter accomplished on LB Ampicillin plates, followed by incubation overnight at 37° C.

Because the resulting colonies comprised mSLO.3/6, the blood overlay screening protocol could not be utilized (i.e., a non-viable colony could also evidence nonhemolytic activity). Accordingly, screening was accomplished using hybridation probes obtained from pUC19-SLO-B cut with BstE II and ECoRV (approximately a 1.1Kb probe), labelled by the random primer labelling method described in *Anal. Biochem.*, 132 6-13(1983).

In order to screen these colonies, pure nitrocellulose transfer membranes (Schleicher & Schuell, Keene, N.H., No. 20440; pore size: 0.45 $\mu$m) were placed onto the plates, and colonies were lifted therefrom. The membranes were subjected to a denaturing buffer (0.5M NaOH; 1.5M NaCl) for 5 min at room temperature. This was followed by addition of a neutralizing buffer (1.5M NaCl; 1M TRIS, pH 8.0). The membranes were then baked for 2 hrs at 80° C., followed by addition thereto of 12ml of. hybridization buffer (5X SSPE; 50% deionized formamide; 5X Denhardts; 100 $\mu$g/ml denatured salmon testes DNA—see Molecular Cloning) and prehybridized for lhr at 37° C. Thereafter, the above-described probes were added therto, and hybridized overnight at 37° C. This was followed by three washings (10 min each) with 10mM $KPO_4$, pH 7.0, 1mM EDTA. The membranes were then exposed to x-ray film overnight at −70° C. Areas indicative of successful hybridization were then used to obtain colonies comprising the mSnO.3/6 subclones.

Screened colonies comprising mSLO.3/6 subclones were innoculted in 12 ml of Superbroth-ampicillin broth. Induction was accomplished by the addition of isoprpyl-$\beta$-D-thiogalactopyranoside ("IPTG"), at a final concentration of 1mM, to the culture broth when the culture broth had an $OD_{600}$ reading of 0.7. 12ml of the resulting solution was centrifuged at 8000 RPM for 10 min at 4° C. and the resulting pellet resuspended in 1.2 ml of PBS/10mM DTT. The resuspended pellet was sonicated for 1.5 min; the protein concetration of the sonicated extract was determined using the BioRad Protein Assay protocol described above. For the extract comprising mSLO.3/6, the protein concentration was 13 mg/ml. This data was used to determine the specific hemolytic activity of the sonicated extract by titer based upon the 50% lyses of 2.5% washed rabbit red blood cell protocol described above.

For purposes of comparing the specific hemolytic activity of mSLO.3/6 with that of rSLO.3 using the pBTac2-JM105 expression system, rSLO.3 was also obtained using this expression system following the specific procedure described above (derived protein concentration of extract comprising rSLO.3—9.3 mg/ml). Results are provided in Table 3:

TABLE 3

| Sonicated Extract ($\mu$g) | | >50% Lysis (+) <50% Lysis (−) | Hemolytic Units per mg extract |
|---|---|---|---|
| mSLO.3/6 | 260. | (−) | |
| | 520. | (−) | |
| | 1040. | (−) | $4.8 \times 10^{-1}$* |
| | 2080 | (−) | |
| rSLO.3 | 0.186 | (−) | |
| | 0.372 | (+) | $2.69 \times 10^{-3}$ |
| | 0.744 | (+) | |
| | 1.116 | (+) | |
| | 4.650 | (+) | |

*Estimated based upon 25% lysis at endpoint which contains 2080 $\mu$g extract per ml of buffer The foregoing data indicates that for the pBTac2 JM105 expression system, the crude extract comprising mSLO.3/6 is approximately 5,600 times less hemolytically active than the crude extract comprising rSLO.3.

EXAMPLE 12

Comparative Analysis of Expression Systems In an effort to compare the relative expression systems vis-a-vis the expression of rSLO.3 and mSLO.3/6, Western blot analysis was conducted on the pellets and supernatants for the pΔ33 vector comprising rSLO.3 and pBTac2 vectors comprising rSLO.3 and mSL0.3/6. Identical protocols were followed for side-by-side comparative studies; each transformed host was innoculated in Superbroth, and respective induction strategies were used, i.e., naladixic acid for pΔ33, and IPTG for pBTac2. FIG. 9 provides the results of the Western blots of the crude extracts from the various materials indicated.

As is evident from FIG. 9 itself, the pΔ33 expression system appears to differ from the pBTac2 system in that the bands for SLO-material, while appearing in approximately the same horizontal lane as with the pBTac2 system, appear to evidence a greater amount of SLO in the pellet compared to the pBTac2 system. In an effort to confirm these trends, the results of FIG. 9 were analyzed by the aforemention Beckman DU 7000 spectrophotometer, and the resulting peaks for SLO-material (as a function of total peak area for both. pellet and supernatant) for each system were compared. These results are summarized below in Table 4:

TABLE 4

| | pΔ33-rSLO.3 | | pBTac2-rSLO.3 | | pBTac2-mSLO.3/6 | |
|---|---|---|---|---|---|---|
| | S | P | S | P | S | P |
| A | 9.23 | 8.14 | 13.71 | 7.01 | 12.44 | 7.22 |
| B | 53 | 47 | 66 | 34 | 63 | 37 |

S - Supernatant
P - Pellet
A - Specific peak area relative to total peak areas for S lane and P lane
B - Percentage of (S + P)

These results indicate that for the pΔ33 system, more SLO is in the pellet compared to the pBTac2 system; nearly twice as much SLO material is in the pBTac2 supernatant than in the pellet, while for the pΔ33 system, approximately the same amount of SLO material is in the supernatant and the pellet.

EXAMPLE 14

Analysis of Specific Hemolytic Activity of Purified mSLO.3/6 and r/SLO.3

As noted, the specific activity and percent hemolytic activity of specific versions of rSLO and mSLO (purifed rSLO.3 and mSLO.3/6 respectively), based upon the "specific activity" of wild-type SLO, are as follows in Table 4:

TABLE 5

| | Wild-Type SLO | rSLO.3 | mSLO.3/6 |
|---|---|---|---|
| Specific Activity (Hemolytic Activity in Hemolytic Units/mg) | a) $1 \times 10^6$<br>b) $1 \times 10^5$ | $3.6 \times 10^4$ | 14 |
| Percent Hemolytic Activity of Wild-Type SLO | a) 100<br>b) 100 | 3.6<br>9 | $1.4 \times 10^{-3}$<br>$3.5 \times 10^{-3}$ |

The foregoing indicates that mSLO.3/6 is about $1.4 \times 10^{-2}$% less hemolytically active than wild-type SLO. I.e., mSLO.3/6 has less than 1% of the hemolytic activity of wild-type SLO.

EXAMPLE 14

In Vivo Toxicity Effects of mSLO.3/6

In order to evaluate in vivo toxicity effects of mSLO.3/6, Balb/c mice were administered undiluted and diluted intravenous injections of mSLO.3/6. Undiluted and diluted control suspension buffer was administered to an equivalent number of mice. To improve the intravenous injections, the mice were warmed under a heat lamp for 20–30 minutes of pre-injection. Approximately 20 mice were used for each condition.

For the undiluted mSLO.3/6, each mouse received an approximate dosage of 17 mg/kg, while for the diluted mSLO.3/6, each mouse received an approximate dosage of 1000 μg/kg. Control solution buffer did not affect the control mice.

128D-122

Aside from minor ruffling for several minutes after injection, none of the mice receiving either diluted or undiluted mSLO.3/6 showed any ill effects from the intravenous administrations. This data supports the specific activity data for purified mSLO.3/6, i.e., the non-hemolytic activity of mSLO.3/6 is evident in that the mice receiving both diluted or undiluted doses thereof did not expire or otherwise evidence any serious side effects.

The foregoing Examples are directed to the generation of an SLO genomic library. As those in the art appreciate, another type of library which is much less complex than a genomic DNA library is a "complementary DNA", or "cDNA", library. cDNA is derived directly from mRNA; therefore, by definition, the cDNA library is comprised of regions of translation. Methods for deriving cDNA libraries based upon mRNA complementary to mSLO DNA are considered to be within the purview of the skilled artisan such that cDNA-based libraries for mSLO are a part of this disclosure.

PROTEIN FOLDING

As the linear arrangement of nucleotides defines a specific codon, the arrangement, or sequence, of amino acids defines the protein, including the particular function thereof. However, while the particular amino acid sequence is important with respect to the identity of the protein, the particular three dimensional shape that the protein exhibits is of similar import. Such specificity in terms of shape, in essence, co-defines the properties of the protein because the shape of the protein enables the protein to specifically interact with other molecules that will only recognize that particular protein shape.

Most proteins spontaneously fold into their correct shape as they are translated within the cell. By treating the protein with certain denaturing solvents, the protein can "unfold" into a flexible chain. When the denaturing agent is removed, portions of the the flexible chain may refold into their original conformation. This is because one of the most important factors governing the folding of a protein is the distribution of polar (hydrophilic, or "water-hating") and non-polar (hydrophobic, or "water-loving") side chains of the amino acids of that protein. Denaturing solvents interfere with the polarity of the amino acid side chains. The following amino acids have polar side chains: Asn; Gln; Ser; Thr; and Tyr. The following amino acids have nonpolar side chains: Gly; Ala; Val; Leu; Iso; Pro; Phe; Met; Trp; and Cys. Amino acids with basic and acidic side chains are very polar. The following amino acids have basis side chains: Lys; Arg; and His. The following amino acids have acidic side chains: Asp and Glu.

The environment in which proteins naturally exist is, by definition, a non-denaturing environment, which is most typically aqueous. Accordingly, the hydrophobic side chains of a protein tend to be pushed together in the interior of the protein molecule, which enables these to avoid contact with the aqueous environment. Polar side chains, on the other hand, tend to arrange themselves near the outside of the protein molecule, where they can interact with water and other polar molecules.

While the molecular mechanisms by which a linear DNA sequence is transcribed and translated into a precise amino acid sequence of the corresponding polypeptide is well understood, exactly how the polypeptide chain folds simultaneously and autonomously into its three-dimensional structure is not clearly understood. The real potential of synthetic DNA, i.e. DNA synthesized via recombinant techniques, will be realized in the area of protein design. In order for this to be realized, however, the mechanism of protein folding well have to be more succinctly clarified. While the general problem of predicting protein structure from the sequence is elusive (principally because no rules have emerged that allow structure to be related to sequence), it is clear that certain portions of the sequence are important to the structure and other portions are relatively unimportant from a structural point of view such that substitutions or modifications can be made at these portions. Accordingly, it is assumed that portions of the sequence of a protein contribute significantly to the stability of the folded protein structure.

While predicting a protein structure from the protein sequence is elusive, proteins, by definition, have unique three-dimensional structures which can be determined. The following methodologies, for example, can be used in the determination of protein structure: Crystallography; Optical Activity, Nuclear Magnetic Resonance Spectroscopy.

a) Crystollagraphy

Proteins are capable of forming crystals. Proteins usually crystallize in a condition of saturation or supersaturation which can be achieved by altering one or more of a number of variables that affect the solubility of the proteins. Thus, by altering the ionic strength of the solution or by utilization of organic polymers, e.g., polyethylene glycol, proteins can be crystallized. Techniques for growing protein crystals are set forth in Narang, S. A. *Protein Engineering: Approaches to the Manipulation of Protein Folding* (Butterworth, Publisher, Stoneham, Mass, 1990), Chpt. 6 (hereinafter "Narang"). The preceding text book is incorporated herein by reference in its entirety. Having crystallized the protein, the techniques of x-ray, neutron, and electron diffraction can be used to determine to structure of the protein, with x-ray diffraction being preferred. The protein structure in the crystal is assumed to be at or near the minimum conformational free energy of the molecule for the crystal form.

b) Optical Activity

The optical activity of polypeptides/proteins due to the asymmetric centers of the amino acids and to the asymmetric conformations thereof, can be utilized to determine the structure of polypeptides/proteins. This asymmetry causes proteins to interact differently with right- and left-circularly polarized light; if the two beams consequently travel at different speeds through the protein, polarized light is rotated. Optical rotatory dispersion ("ORD") is the dependence of this rotation upon wavelength. In a wavelength region where the protein molecule does not absorb light, the rotation varies gradually with wavelength, but in an absorbance region, the rotation first increases sharply in one direction, falls to zero at the absorption maximum, and then rises sharply in the opposite direction. There will also be unequal absorption of left- and right-circularly polarized light; this is referred to as circular dichroism ("CD"). Both CD and OES spectra of a protein are very sensitive to the structural conformation thereof. Folded proteins generally have significant optical activity in the near-UV region (250-300nm).

c) Nuclear Magnetic Resonance Spectroscopy

Nuclear Magnetic Resonance Spectroscopy, using, e.g., $^1H$, $^{13}C$, $^{15}N$, $^{13}P$ or $^2H$, has proven to be of great use in studying protein structure in solution. Focusing on 1H, each hydrogen atom in a molecule has a nuclear magnetic spin, i.e. the nuclei of the atom act like tiny magnets. In the absence of an external magnetic field, the magnetic moments of the protons are randomly oriented. In a Nuclear Magnetic Resonance experiment, a strong external magnetic field is applied to the sample along a specified direction, resulting in a net alignment of the magnetic moments and a net macroscopic magnetization along the specified directional axis; a short radio-frequency pulse of appropriate strength is then applied, knocking the magnetization vector away from this axis. As the magnetization recovers, a transient radio-frequency signal is recorded as a function of time. A fourier-transform of this signal then yields a frequency spectrum. Each proton in the molecule gives rise to a peak in this spectrum occurring at some characteristic resonance frequency determined by the local electronic environment of that proton. The resonance frequency of a particular proton is called its "chemical shift" and is measured as an offset from some reference frequency. Structured information from NMR is derived from the nuclear Overhauser effect ("NOE", which determines whether a pair of protons are near each other in space) and the coupling constants of protons that are separated by three or fewer chemical bonds. NOE and coupling constants provide one-dimensional data; two-dimensional data is provided by inter alia nuclear Overhauser enhancement spectroscopy (NOESY) and two-dimensional correlation spectroscopy (COSY); and from such data, three-dimensional protein structures can be determined.

In view of the foregoing information set forth with respect to determination of the three-dimensional structure of protein molecules, the following claims directed to DNA macromolecules and amino acids inherently include the three dimensional structures associated with the protein molecules expressed thereby.

The Examples herein are not to be construed as limited to specific vectors, plasmids and host cells which are preferred. The mSLO described herein is not to be construed as limited solely to the preferred mSLO designated mSLO.3/6. Similarly, the preferred mSLO.3/6 in no way constitute an admission, either actual or implied, that the DNA and amino acid sequences thereof are the only DNA and amino acid sequences to which Applicant is entitled. Applicant is entitled to the full breadth of protection under applicable patent laws.

For purposes of claiming materials by designation, JM105 transformed with plasmids comprising pBTac2 DNA—mSL0.3/6 and AR120 transformed with vectors comprising pΔ33—mSLO.3/6 were deposited on Aug. 23, 1991 with the American Type Culture Collection (ATCC), 12301 Parklawn Drive, Rockville, Maryland, 20852, under the provisions of the Budapest Treaty for the International Recognition of the Deposit of Microorganisms for the Purpose of Patent Procedure. These were tested by the ATCC on Aug. 27, 1991, and determined to both be viable. The ATCC has assigned the deposit numbers ATCC 68678 and ATCC 68676, respectively, to these materials.

Having identified a single nucleotide (and aminoacid) difference between rSLO.3 and mSLO.3/6, those skilled in the art can readily prepare the DNA sequence set forth in FIG. 1 using various methodologies known to those in the art, e.g., wild-type SLO subjected to the process described in, e.g., U.S. Pat. No. 4,351,901 ("Method for single nucleotide alteration"), which is incorporated herein by reference. Other methodologies for nucleotide and amino acid substitution, terminal and intermediate alterations and deletions will be readily apparent to those skilled in the art. Furthermore, as the DNA synthesis art progresses such that oligonucleotides having the length of the DNA sequence of FIG. 1 can be rapidly obtained, one can synthesize that sequence as appropriate with such advances in the art.

Additionally, because Applicant has discovered, inter alia, that the single nucleotide substitution identified in FIG. 1 (which in turn leads to a single amino acid change as set forth in FIG. 2) has reduced the hemolytic activity of the SLO variant as described, those skilled in the art can readily obtain fragments of that DNA sequence (e.g., via nucleotide deletion) such that the fragment continues to maintain at least one epitopic site characteristic of wild-type SLO and maintains nonhemolytic characteristics. Furthermore, and as noted, conservative substitutions of nucleotides can be made without concomitant changes in the amino acid sequence, as those in the art understand and appreciate. For example, "computerized back translation" techniques can be used, whereby the amino acid sequence is analyzed by a computer and the computer determines the optimum nucleotides to utilize in the codons necessary to encode such amino acids. Additionally, DNA sequences preferably evidencing 80% homology with the DNA sequence of FIG. 1, preferably 85%, and most preferably 90% homology with that sequence are considered to fall within the scope of the invention.

Because the screening of SLO variants can be readily accomplished using the above-described blood overlay technique, numerous SLO variant candidates can be rapidly evaluated. Accordingly, having defined the specific substitution that has led to the specific SLO variant, those skilled in the art can readily use this advance in the art to derive SLO variant analog candidates, rapidly screen these candidates for indications of nonhemolytic activity, and determine the nucleic acid and amino acid sequences of analogs which fall within Applicant's definition of mSLO.

Accordingly: while the Examples herein are directed to a specific SLO variant, mSLO.3/6; because, statistically speaking, this variant has no hemolytic activity compared to wild-type SLO; and because having had this advance in the art placed in their possession, those in the art can utilize techniques known to the art to adapt this advance to their own ends, Applicant's invention is seen to comprehend SLO variants having the characteristics as defined, and is not limited to the specific variant disclosed in the Examples.

Although the present invention has been described in considerable detail with regard to certain preferred embodiments thereof, other embodiments within the scope of the teachings of the present invention are possible. As such, while the production of a specific SLO variant has been described in detail, this is to be construed as an exemplar. Accordingly, neither the disclosure, nor the claims to follow, are intended, nor should be construed to be, limited by the descriptions of the preferred embodiments contained herein.

What is claimed is:

1. A protein variant of Streptolysin O comprising amino acids 1 through 473, inclusive, of the amino acid sequence set forth in FIG. 2 SEQ ID NO:2.

* * * * *